(12) United States Patent
Bergbrede et al.

(10) Patent No.: US 10,883,137 B2
(45) Date of Patent: Jan. 5, 2021

(54) METHOD TO DETECT ACTIVITY OF A POLYMERASE

(71) Applicants: MAX-PLANCK-GESELLSCHAFT ZUR FÖRDERUNG DER WISSENSCHAFTEN E.V., Munich (DE); LEAD DISCOVERY CENTER GMBH, Dortmund (DE)

(72) Inventors: Tim Bergbrede, Dortmund (DE); Nils-Göran Larsson, Cologne (DE); Claes Gustafsson, Mölndal (SE); Maria Falkenberg-Gustafsson, Mölndal (SE)

(73) Assignees: MAX-PLANCK-GESELLSCHAFT ZUR FÖRDERUNG DER WISSENSCHAFTEN E.V., Munich (DE); LEAD DISCOVERY CENTER GMBH, Dortmund (DE)

( * ) Notice: Subject to any disclaimer, the term of this patent is extended or adjusted under 35 U.S.C. 154(b) by 306 days.

(21) Appl. No.: 15/577,028

(22) PCT Filed: May 30, 2016

(86) PCT No.: PCT/EP2016/062198
§ 371 (c)(1),
(2) Date: Nov. 27, 2017

(87) PCT Pub. No.: WO2016/193231
PCT Pub. Date: Dec. 8, 2016

(65) Prior Publication Data
US 2018/0142285 A1    May 24, 2018

(30) Foreign Application Priority Data
May 29, 2015  (EP) .................. 15169966

(51) Int. Cl.
*C12Q 1/6818*  (2018.01)
*C12Q 1/68*  (2018.01)
(Continued)

(52) U.S. Cl.
CPC .......... *C12Q 1/6818* (2013.01); *C12Q 1/48* (2013.01); *C12Q 1/68* (2013.01); *C12Q 1/6825* (2013.01);
(Continued)

(58) Field of Classification Search
CPC .................................. C12Q 1/6818
(Continued)

(56) References Cited

U.S. PATENT DOCUMENTS

2012/0070838 A1*  3/2012  Xi ............... C12Q 1/686
                                                    435/6.12
2012/0135874 A1*  5/2012  Wang ............ C12Q 1/6844
                                                    506/9

FOREIGN PATENT DOCUMENTS

WO   2010/036359   4/2010
WO   2012/024639   2/2012

OTHER PUBLICATIONS

Sei-Iida et al., Real-time monitoring of in vitro transcriptional RNA synthesis using fluorescence resonance energy transfer, Jun. 15, 2000, Nucleic Acids Research, 28(12) (Year: 2000).*

(Continued)

*Primary Examiner* — Holly Kipouros
(74) *Attorney, Agent, or Firm* — Kowert, Hood, Munyon, Rankin & Goetzel, P.C.; Mark R. DeLuca

(57) ABSTRACT

The present invention relates to methods for detection of nucleotide polymerase activity and methods of detecting compounds that modulate nucleotide polymerase activity, by detecting product formation of the nucleotide polymerase to be tested based on determination of close proximity of two
(Continued)

labeled nucleotide probes able to bind the product of the nucleotide polymerase. It is preferred that proximity dependent energy transfer, such as forster resonance energy transfer, between said labeled nucleotide probes is determined. The invention further provides kits comprising components for carrying out the inventive methods for detection of nucleotide polymerase activity.

23 Claims, 11 Drawing Sheets

Specification includes a Sequence Listing.

(51) Int. Cl.
    *C12Q 1/6825*     (2018.01)
    *G01N 33/542*     (2006.01)
    *G01N 33/58*     (2006.01)
    *C12Q 1/48*     (2006.01)

(52) U.S. Cl.
    CPC ......... *G01N 33/542* (2013.01); *G01N 33/582* (2013.01); *G01N 2333/91245* (2013.01)

(58) Field of Classification Search
    USPC ...................................................... 435/289.1
    See application file for complete search history.

(56) References Cited

OTHER PUBLICATIONS

Krebs et al., Novel FRET-Based Assay to Detect Reverse Transcriptase Activity Using Modified dUTP Analogues, 2008, Bioconjugate Chem., 19, pp. 185-191 (Year: 2008).*

Fodor et al, Walleye dermal sarcoma virus reverse transcriptase is temperature sensitive, 2002, Journal of General Virology, 83, pp. 1361-1365) (Year: 2002).*

Nazarenko et al. "A Closed Tube Format for Amplification and Detection of DNA Based Energy Transfer" Nucleic Acids Research, vol. 25, No. 12, Jan. 1, 1997, pp. 2516-2521.

Gabourdes et al. "A Homogenous Tine-Resolved Fluorescence Detection of Telomerase Activity" Analytical Biochemistry, vol. 333, No. 1, Oct. 1, 2004, pp. 105-113.

Krebs et al. "Novel FRET-Based Assay to Detect Reverse Transcriptase Activity Using Modified dUTP Analogues" Bioconjugate Chemistry, vol. 19, No. 1, Jan. 1, 2008, pp. 185-191. Abstract.

Kutyavin et al. "New Approach to Real-Time Nucleic Acids Detection: Folding Polymerase Chain Reaction Amplicons Into a Secondary Structure to Improve Cleavage of Forster Resonance Energy Transfer Probes in 5′-Nuclease Assays" Nucleic Acids Research, vol. 38, No. 5, May 1, 2010, pp. e29.1-e29.12.

International Search Report and Written Opinion for PCT/EP2016/062198 dated Jul. 11, 2016.

* cited by examiner

Figure 6 plateID1073895494

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| A | 0.52 | 0.53 | 0.52 | 0.51 | 0.52 | 0.52 | 0.52 | 0.56 | 0.55 | 0.53 | 0.53 | 0.55 | 0.53 | 0.54 | 0.53 | 0.54 |
| B | 0.51 | 0.50 | 0.51 | 0.53 | 0.52 | 0.52 | 0.49 | 0.52 | 0.53 | 0.53 | 0.53 | 0.56 | 0.54 | 0.53 | 0.54 | 0.53 |
| C | 0.53 | 0.52 | 0.52 | 0.54 | 0.53 | 0.52 | 0.55 | 0.53 | 0.54 | 0.54 | 0.53 | 0.53 | 0.54 | 0.55 | 0.55 | 0.53 |
| D | 0.51 | 0.50 | 0.53 | 0.52 | 0.53 | 0.53 | 0.56 | 0.54 | 0.54 | 0.55 | 0.55 | 0.54 | 0.56 | 0.55 | 0.54 | 0.55 |
| E | 0.53 | 0.53 | 0.53 | 0.55 | 0.56 | 0.56 | 0.54 | 0.54 | 0.54 | 0.55 | 0.58 | 0.56 | 0.57 | 0.58 | 0.57 | 0.57 |
| F | 0.52 | 0.53 | 0.52 | 0.53 | 0.54 | 0.55 | 0.55 | 0.54 | 0.55 | 0.55 | 0.56 | 0.57 | 0.55 | 0.56 | 0.56 | 0.55 |
| G | 0.54 | 0.54 | 0.55 | 0.53 | 0.55 | 0.55 | 0.55 | 0.57 | 0.56 | 0.58 | 0.58 | 0.56 | 0.56 | 0.57 | 0.56 | 0.58 |
| H | 0.54 | 0.53 | 0.53 | 0.54 | 0.54 | 0.52 | 0.57 | 0.56 | 0.57 | 0.56 | 0.57 | 0.57 | 0.56 | 0.60 | 0.57 | 0.56 |
| I | 0.53 | 0.55 | 0.53 | 0.54 | 0.54 | 0.56 | 0.56 | 0.55 | 0.56 | 0.56 | 0.56 | 0.58 | 0.56 | 0.57 | 0.56 | 0.57 |
| J | 0.51 | 0.54 | 0.54 | 0.56 | 0.54 | 0.54 | 0.55 | 0.57 | 0.57 | 0.56 | 0.55 | 0.54 | 0.56 | 0.57 | 0.56 | 0.57 |
| K | 0.53 | 0.52 | 0.56 | 0.54 | 0.57 | 0.55 | 0.55 | 0.48 | 0.56 | 0.55 | 0.58 | 0.57 | 0.57 | 0.57 | 0.58 | 0.57 |
| L | 0.55 | 0.52 | 0.55 | 0.55 | 0.55 | 0.53 | 0.56 | 0.55 | 0.55 | 0.56 | 0.56 | 0.56 | 0.58 | 0.57 | 0.56 | 0.56 |
| M | 0.56 | 0.59 | 0.59 | 0.60 | 0.58 | 0.57 | 0.58 | 0.61 | 0.58 | 0.60 | 0.60 | 0.62 | 0.60 | 0.62 | 0.60 | 0.62 |
| N | 0.55 | 0.55 | 0.57 | 0.56 | 0.57 | 0.57 | 0.60 | 0.60 | 0.60 | 0.58 | 0.59 | 0.59 | 0.61 | 0.60 | 0.61 | 0.60 |
| O | 0.56 | 0.55 | 0.59 | 0.58 | 0.58 | 0.59 | 0.59 | 0.61 | 0.60 | 0.60 | 0.62 | 0.62 | 0.63 | 0.62 | 0.64 | 0.60 |
| P | 0.57 | 0.58 | 0.58 | 0.58 | 0.58 | 0.58 | 0.58 | 0.59 | 0.60 | 0.60 | 0.61 | 0.61 | 0.66 | 0.60 | 0.62 | 0.61 |
| Q | 0.58 | 0.57 | 0.58 | 0.60 | 0.57 | 0.60 | 0.60 | 0.59 | 0.59 | 0.60 | 0.59 | 0.62 | 0.63 | 0.62 | 0.62 | 0.60 |
| R | 0.54 | 0.58 | 0.58 | 0.58 | 0.59 | 0.58 | 0.61 | 0.61 | 0.59 | 0.59 | 0.60 | 0.60 | 0.61 | 0.60 | *0.11* | 0.63 |
| S | 0.56 | 0.58 | 0.57 | 0.56 | 0.57 | 0.57 | 0.59 | 0.62 | 0.60 | 0.60 | 0.60 | 0.60 | 0.61 | 0.62 | 0.61 | 0.59 |
| T | 0.55 | 0.53 | 0.55 | 0.57 | 0.58 | 0.60 | 0.59 | 0.58 | 0.62 | 0.59 | 0.59 | 0.61 | 0.59 | 0.61 | 0.60 | 0.59 |
| U | 0.56 | 0.60 | 0.59 | 0.58 | 0.58 | 0.57 | 0.58 | 0.60 | 0.61 | 0.60 | 0.61 | 0.61 | 0.61 | 0.61 | 0.62 | 0.62 |
| V | 0.58 | 0.57 | 0.57 | 0.58 | 0.58 | 0.59 | 0.60 | 0.59 | 0.60 | 0.58 | 0.59 | 0.60 | 0.62 | 0.59 | 0.63 | 0.62 |
| W | 0.55 | 0.57 | 0.58 | 0.59 | 0.57 | 0.58 | 0.60 | 0.61 | 0.60 | 0.60 | 0.61 | 0.61 | 0.60 | 0.61 | 0.61 | 0.61 |
| X | 0.57 | 0.56 | 0.58 | 0.57 | 0.59 | 0.58 | 0.59 | 0.61 | 0.58 | 0.59 | 0.60 | 0.60 | 0.60 | 0.59 | 0.63 | 0.61 |
| Y | 0.57 | 0.58 | 0.58 | 0.60 | 0.58 | 0.59 | 0.60 | 0.60 | 0.61 | 0.61 | 0.61 | 0.63 | 0.62 | 0.62 | 0.62 | 0.63 |
| Z | 0.56 | 0.58 | 0.56 | 0.60 | 0.59 | 0.59 | 0.61 | 0.60 | 0.60 | 0.61 | 0.63 | 0.59 | 0.61 | 0.60 | 0.63 | 0.62 |
| AA | 0.58 | 0.58 | 0.58 | 0.57 | 0.59 | 0.59 | 0.60 | 0.60 | 0.60 | 0.62 | 0.63 | 0.62 | 0.62 | 0.61 | 0.63 | 0.63 |
| AB | 0.56 | 0.56 | 0.57 | 0.59 | 0.59 | 0.59 | 0.61 | 0.58 | 0.60 | 0.61 | 0.59 | 0.61 | 0.63 | 0.63 | 0.62 | 0.63 |
| AC | 0.56 | 0.57 | 0.56 | 0.58 | 0.57 | 0.58 | 0.58 | 0.60 | 0.59 | 0.61 | 0.62 | 0.61 | 0.62 | 0.62 | 0.62 | 0.61 |
| AD | 0.56 | 0.56 | 0.54 | 0.58 | 0.58 | 0.59 | 0.59 | 0.44 | 0.60 | 0.59 | 0.62 | 0.64 | 0.60 | 0.62 | 0.62 | 0.65 |
| AE | 0.55 | 0.56 | 0.54 | 0.58 | 0.58 | 0.57 | 0.58 | 0.59 | 0.61 | 0.59 | 0.60 | 0.61 | 0.61 | 0.61 | 0.60 | 0.61 |
| AF | 0.54 | 0.56 | 0.57 | 0.56 | 0.55 | 0.55 | 0.57 | 0.57 | 0.58 | 0.58 | 0.60 | 0.61 | 0.59 | 0.61 | 0.60 | 0.60 |

Figure 6 continued neg.control   pos.control

| 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| 0.53 | 0.54 | 0.54 | 0.54 | 0.54 | 0.53 | *0.06* | *0.06* | 0.53 | 0.54 | 0.52 | 0.55 | 0.53 | 0.55 | 0.53 | 0.55 |
| 0.53 | 0.52 | 0.54 | 0.54 | 0.54 | 0.53 | *0.06* | *0.06* | 0.54 | 0.55 | 0.55 | 0.54 | 0.54 | 0.55 | 0.54 | 0.55 |
| 0.55 | 0.55 | 0.56 | 0.55 | 0.54 | 0.54 | *0.06* | *0.06* | 0.54 | 0.54 | 0.57 | 0.57 | 0.55 | 0.56 | 0.56 | 0.56 |
| 0.53 | 0.54 | 0.56 | 0.54 | 0.54 | 0.54 | *0.06* | *0.06* | 0.55 | 0.54 | 0.56 | 0.57 | 0.55 | 0.56 | 0.56 | 0.55 |
| 0.57 | 0.56 | 0.58 | 0.57 | 0.58 | 0.58 | *0.06* | *0.06* | 0.59 | 0.59 | 0.58 | 0.59 | 0.58 | 0.59 | 0.57 | 0.57 |
| 0.57 | 0.57 | 0.57 | 0.55 | 0.56 | 0.57 | *0.06* | *0.06* | 0.55 | 0.55 | 0.57 | 0.55 | 0.58 | 0.55 | 0.56 | 0.61 |
| 0.57 | 0.55 | 0.58 | 0.59 | 0.54 | 0.57 | *0.06* | *0.06* | 0.58 | 0.58 | 0.60 | 0.54 | 0.57 | 0.56 | 0.59 | 0.57 |
| 0.58 | 0.58 | 0.56 | 0.57 | 0.55 | 0.56 | *0.06* | *0.06* | 0.58 | 0.58 | 0.57 | 0.56 | 0.57 | 0.56 | 0.58 | 0.56 |
| 0.55 | 0.59 | 0.57 | 0.56 | 0.57 | 0.57 | *0.06* | *0.06* | 0.56 | 0.56 | 0.57 | 0.56 | 0.58 | 0.60 | 0.59 | 0.58 |
| 0.54 | 0.56 | 0.58 | 0.57 | 0.56 | 0.57 | *0.06* | *0.06* | 0.57 | 0.57 | 0.57 | 0.56 | 0.58 | 0.57 | 0.58 | 0.57 |
| 0.58 | 0.57 | 0.57 | 0.56 | 0.58 | 0.57 | *0.06* | *0.06* | 0.54 | 0.56 | 0.58 | 0.57 | 0.57 | 0.60 | 0.59 | 0.57 |
| 0.57 | 0.57 | 0.56 | 0.56 | 0.57 | 0.56 | *0.06* | *0.06* | 0.57 | 0.57 | 0.57 | 0.58 | 0.61 | 0.58 | 0.59 | 0.57 |
| 0.60 | 0.58 | 0.61 | 0.60 | 0.61 | 0.61 | *0.06* | *0.06* | 0.62 | 0.61 | 0.61 | 0.61 | 0.61 | 0.61 | 0.61 | 0.62 |
| 0.60 | 0.63 | 0.60 | 0.63 | 0.60 | 0.59 | *0.06* | *0.06* | 0.63 | 0.61 | 0.63 | 0.63 | 0.62 | 0.63 | 0.61 | 0.61 |
| 0.64 | 0.63 | 0.61 | 0.61 | 0.62 | 0.61 | *0.06* | *0.06* | 0.61 | 0.62 | 0.63 | 0.62 | 0.61 | 0.62 | 0.60 | 0.62 |
| 0.60 | 0.61 | 0.61 | 0.62 | 0.62 | 0.59 | *0.06* | *0.06* | 0.63 | 0.61 | 0.62 | 0.61 | 0.62 | 0.64 | 0.61 | 0.63 |
| 0.64 | 0.63 | 0.63 | 0.61 | 0.60 | 0.61 | *0.06* | *0.06* | 0.61 | 0.60 | 0.63 | 0.61 | 0.61 | 0.62 | 0.63 | 0.61 |
| 0.61 | 0.61 | 0.61 | 0.63 | 0.61 | 0.60 | *0.06* | *0.07* | 0.62 | 0.63 | 0.63 | 0.62 | 0.63 | 0.62 | 0.62 | 0.61 |
| 0.62 | 0.64 | 0.61 | 0.62 | 0.61 | 0.62 | *0.06* | *0.06* | 0.62 | 0.62 | 0.62 | 0.63 | 0.62 | 0.63 | 0.62 | 0.63 |
| 0.61 | 0.62 | 0.61 | 0.53 | 0.60 | 0.61 | *0.06* | *0.06* | 0.60 | 0.62 | 0.61 | 0.62 | 0.62 | 0.57 | 0.62 | 0.62 |
| 0.61 | 0.60 | 0.63 | 0.64 | 0.61 | 0.63 | *0.06* | *0.06* | 0.63 | 0.61 | 0.64 | 0.62 | 0.64 | 0.62 | 0.64 | 0.64 |
| 0.61 | 0.62 | 0.58 | 0.63 | 0.62 | 0.63 | *0.05* | *0.06* | 0.61 | 0.64 | 0.58 | 0.62 | 0.61 | 0.61 | 0.64 | 0.63 |
| 0.61 | 0.60 | 0.62 | 0.63 | 0.62 | 0.62 | *0.06* | *0.06* | 0.62 | 0.63 | 0.62 | 0.63 | 0.63 | 0.62 | 0.62 | 0.62 |
| 0.63 | 0.60 | 0.62 | 0.63 | 0.62 | 0.62 | *0.05* | *0.06* | 0.62 | 0.64 | *0.26* | 0.63 | 0.63 | 0.62 | 0.62 | 0.64 |
| 0.64 | 0.62 | 0.64 | 0.63 | 0.64 | 0.63 | *0.06* | *0.06* | 0.63 | 0.64 | 0.64 | 0.62 | 0.62 | 0.66 | 0.62 | 0.63 |
| 0.63 | 0.61 | 0.64 | 0.64 | 0.62 | 0.64 | *0.06* | *0.06* | 0.64 | 0.64 | 0.64 | 0.64 | 0.64 | 0.63 | 0.62 | 0.63 |
| 0.61 | 0.65 | 0.63 | 0.63 | 0.64 | 0.63 | *0.06* | *0.06* | 0.65 | 0.63 | 0.63 | 0.63 | 0.63 | 0.64 | 0.63 | 0.63 |
| 0.63 | 0.62 | 0.62 | 0.64 | 0.63 | 0.63 | *0.06* | *0.06* | 0.63 | 0.64 | 0.63 | 0.64 | 0.64 | 0.63 | 0.65 | 0.63 |
| 0.62 | 0.61 | 0.64 | 0.63 | 0.62 | 0.62 | *0.06* | *0.06* | 0.64 | 0.64 | 0.64 | 0.63 | 0.64 | 0.64 | 0.62 | 0.62 |
| 0.62 | 0.61 | 0.61 | 0.62 | 0.62 | 0.62 | *0.06* | *0.06* | 0.66 | 0.63 | 0.64 | 0.64 | 0.62 | 0.62 | 0.64 | 0.63 |
| 0.61 | 0.63 | 0.63 | 0.62 | 0.61 | 0.62 | *0.06* | *0.06* | 0.63 | 0.62 | 0.61 | 0.63 | 0.63 | 0.63 | 0.63 | 0.62 |
| 0.61 | 0.62 | 0.64 | 0.62 | 0.59 | 0.61 | *0.05* | *0.06* | 0.64 | 0.62 | 0.60 | 0.62 | 0.62 | 0.61 | 0.62 | 0.62 |

Figure 6 continued

| 33 | 34 | 35 | 36 | 37 | 38 | 39 | 40 | 441 | 42 | 43 | 44 | 45 | 46 | 47 | 48 |
|---|---|---|---|---|---|---|---|---|---|---|---|---|---|---|---|
| 0.54 | 0.54 | 0.55 | 0.50 | 0.52 | 0.54 | 0.53 | 0.54 | 0.52 | 0.52 | 0.52 | *0.21* | 0.52 | 0.52 | 0.52 | 0.51 |
| 0.53 | 0.54 | 0.54 | 0.54 | 0.54 | 0.54 | 0.54 | 0.55 | 0.55 | 0.54 | 0.53 | 0.46 | 0.50 | 0.53 | 0.52 | *0.31* |
| 0.55 | 0.55 | 0.57 | 0.55 | 0.56 | 0.53 | 0.54 | 0.55 | 0.55 | 0.55 | 0.54 | 0.53 | 0.54 | 0.55 | 0.53 | 0.53 |
| 0.55 | 0.55 | 0.56 | 0.55 | 0.56 | 0.54 | 0.56 | 0.55 | 0.57 | 0.53 | 0.55 | 0.55 | 0.53 | 0.52 | 0.53 | 0.51 |
| 0.57 | 0.56 | 0.59 | 0.57 | 0.57 | 0.57 | 0.57 | 0.56 | 0.57 | 0.56 | 0.54 | 0.55 | 0.54 | 0.55 | 0.55 | 0.54 |
| 0.57 | 0.56 | 0.57 | 0.56 | 0.55 | 0.57 | 0.58 | 0.59 | 0.56 | 0.57 | 0.56 | 0.55 | 0.56 | 0.57 | 0.54 | 0.55 |
| 0.57 | 0.56 | 0.57 | 0.56 | 0.58 | 0.58 | 0.56 | 0.57 | 0.58 | 0.55 | 0.55 | 0.57 | 0.54 | 0.55 | 0.54 | 0.55 |
| 0.56 | 0.56 | 0.55 | 0.56 | 0.60 | 0.56 | 0.58 | 0.55 | 0.58 | 0.57 | 0.56 | 0.56 | 0.55 | 0.56 | 0.54 | 0.54 |
| 0.56 | 0.56 | 0.56 | 0.57 | 0.58 | 0.59 | 0.55 | 0.57 | 0.58 | 0.57 | 0.57 | 0.55 | 0.56 | 0.57 | 0.54 | 0.55 |
| 0.62 | 0.57 | 0.56 | 0.57 | 0.58 | 0.57 | 0.58 | 0.56 | 0.56 | 0.57 | 0.56 | 0.56 | 0.56 | 0.57 | 0.55 | 0.56 |
| 0.57 | 0.55 | 0.60 | 0.56 | 0.58 | 0.59 | 0.57 | 0.57 | 0.57 | 0.56 | 0.57 | 0.56 | 0.55 | 0.55 | 0.56 | 0.54 |
| 0.57 | 0.55 | 0.57 | 0.59 | 0.57 | 0.57 | 0.58 | 0.57 | 0.56 | 0.58 | 0.57 | 0.58 | 0.56 | 0.55 | 0.55 | 0.55 |
| 0.61 | 0.62 | 0.63 | 0.61 | 0.60 | 0.63 | 0.61 | 0.61 | 0.59 | 0.59 | 0.63 | 0.54 | 0.61 | 0.60 | 0.58 | 0.56 |
| 0.62 | 0.62 | 0.62 | 0.61 | 0.62 | 0.60 | 0.62 | 0.62 | 0.61 | 0.62 | 0.60 | 0.62 | 0.59 | 0.58 | 0.58 | 0.57 |
| 0.62 | 0.61 | 0.61 | 0.63 | 0.61 | 0.61 | 0.60 | 0.61 | 0.60 | 0.60 | 0.62 | 0.61 | 0.60 | 0.60 | 0.60 | 0.59 |
| 0.65 | 0.63 | 0.61 | 0.62 | 0.60 | 0.60 | 0.62 | 0.62 | 0.61 | 0.62 | 0.60 | 0.61 | 0.62 | 0.58 | 0.60 | 0.54 |
| 0.64 | 0.63 | 0.62 | 0.61 | 0.63 | 0.63 | 0.64 | 0.61 | 0.59 | 0.61 | 0.60 | 0.61 | 0.59 | 0.63 | 0.59 | 0.59 |
| 0.62 | 0.63 | 0.61 | 0.62 | 0.61 | 0.60 | 0.60 | 0.62 | 0.65 | 0.61 | 0.61 | 0.61 | 0.60 | 0.58 | 0.57 | 0.58 |
| 0.62 | 0.62 | 0.58 | 0.62 | 0.62 | 0.62 | 0.59 | 0.62 | 0.60 | 0.62 | 0.61 | 0.62 | 0.59 | 0.60 | 0.58 | 0.57 |
| 0.64 | 0.63 | 0.63 | 0.61 | 0.62 | 0.61 | 0.61 | 0.61 | 0.61 | 0.61 | 0.59 | 0.60 | 0.59 | 0.58 | 0.60 | *0.15* |
| 0.62 | 0.62 | 0.62 | 0.64 | 0.65 | 0.62 | 0.61 | 0.60 | 0.63 | 0.62 | 0.63 | 0.60 | 0.61 | 0.59 | 0.58 | 0.58 |
| 0.60 | 0.61 | 0.63 | 0.62 | 0.63 | 0.61 | 0.60 | 0.61 | 0.62 | 0.62 | 0.61 | 0.62 | 0.61 | 0.59 | 0.60 | 0.61 |
| 0.63 | 0.64 | 0.62 | 0.60 | 0.62 | 0.63 | 0.61 | 0.62 | 0.61 | 0.61 | 0.61 | 0.61 | 0.62 | 0.60 | 0.59 | 0.59 |
| 0.61 | 0.62 | 0.63 | 0.62 | 0.63 | 0.63 | 0.58 | 0.61 | 0.61 | 0.61 | 0.64 | 0.60 | 0.63 | 0.58 | 0.58 | 0.54 |
| 0.62 | 0.63 | 0.64 | 0.62 | 0.64 | 0.68 | 0.61 | 0.63 | 0.61 | 0.60 | 0.62 | 0.60 | 0.60 | 0.62 | 0.61 | 0.59 |
| 0.64 | 0.67 | 0.65 | 0.64 | 0.63 | 0.65 | 0.62 | 0.62 | 0.62 | 0.60 | 0.62 | 0.60 | 0.61 | 0.61 | 0.59 | 0.60 |
| 0.63 | 0.65 | 0.66 | 0.64 | 0.62 | 0.64 | 0.62 | 0.63 | 0.61 | 0.64 | 0.64 | 0.61 | 0.61 | 0.58 | 0.59 | 0.59 |
| 0.66 | 0.65 | 0.62 | 0.63 | 0.64 | 0.64 | 0.63 | 0.64 | 0.64 | 0.61 | 0.63 | 0.64 | 0.61 | 0.60 | 0.56 | 0.59 |
| 0.63 | 0.66 | 0.64 | 0.62 | 0.63 | 0.62 | 0.62 | 0.62 | 0.62 | 0.61 | 0.62 | 0.60 | 0.59 | 0.60 | 0.62 | 0.56 |
| 0.65 | 0.63 | 0.65 | 0.64 | 0.61 | 0.61 | 0.61 | 0.62 | 0.60 | 0.61 | 0.62 | 0.64 | 0.61 | 0.60 | 0.58 | 0.60 |
| 0.61 | 0.63 | 0.62 | 0.61 | 0.63 | 0.60 | 0.62 | 0.61 | 0.62 | 0.61 | 0.59 | 0.62 | 0.58 | 0.59 | 0.59 | 0.57 |
| 0.62 | 0.60 | 0.61 | 0.62 | 0.60 | 0.62 | 0.61 | 0.61 | 0.59 | 0.58 | 0.61 | 0.59 | 0.57 | 0.58 | 0.59 | 0.57 | dose-dependent inhibition of T7-RNA polymerase
$IC_{50} = 28.5$ µM

METHOD TO DETECT ACTIVITY OF A POLYMERASE

The present invention relates to methods for detection of nucleotide polymerase activity and methods of detecting compounds that modulate nucleotide polymerase activity, by detecting product formation of the nucleotide polymerase to be tested based on determination of close proximity of two labeled nucleotide probes able to bind the product of the nucleotide polymerase. It is preferred that proximity dependent energy transfer, such as förster resonance energy transfer, between said labeled nucleotide probes is determined. The invention further provides kits comprising components for carrying out the inventive methods for detection of nucleotide polymerase activity.

Enzymes responsible for synthesis of strands or polymers of nucleic acids are referred to as polymerases or nucleotide polymerases; both terms are synonymously used herein. DNA polymerase and RNA polymerase assemble deoxyribonucleic acid (DNA) and ribonucleic acid (RNA) molecules, respectively, using base-pairing interactions between specific nucleobases. Thereby used primary nucleobases are cytosine, guanine, adenine, thymine and uracil, abbreviated as C, G, A, T, and U, respectively.

Polymerases are enzymes used by all living organisms to catalyze the polymerization of nucleotides. They are necessary for multiplication of genetic information in the process of replication. Furthermore, their function is necessary for transcription of genes during the initial stages of gene expression. In addition, polymerases are used by scientists as a common tool in molecular biology, such as in a polymerase chain reaction (PCR).

As long as scientists have used polymerases, inhibitors have been an obstacle to success, in particular when using forensic sample types and variety of sampling conditions. Increasing the activity of polymerases may be useful to improve microbiological technologies (such as increasing sensitivity or stability). In general modulation of polymerase is of high interest in the field of molecular biology.

Furthermore, polymerases are ideal targets for drug therapy. Thus, inhibitors specific for prokaryotic polymerases are used as antibiotic agents. One strategy of anti-viral therapy is to develop inhibitors of viral nucleotide polymerases (reverse transcriptase or RNA dependent DNA polymerase). There are also therapeutic approaches for cancer based on modulation of specific polymerases. Such modulators may stimulate or inhibit polymerase activity, but can also affect specific aspects of polymerase function, for instance processivity.

Several inherited forms of mitochondrial DNA (mtDNA) depletion have been described. Depletion of mtDNA may result from deficient activity of mtDNA polymerase y. Thus, methods for detection of nucleotide polymerase activity may also be reliable diagnostic assays useful in diagnosing mtDNA depletion syndromes Therefore there is an urgent need to provide methods for detection of nucleotide polymerase activity and especially methods of detecting compounds that modulate nucleotide polymerase activity. Ideally, these methods are adaptable to diverse polymerases and can be carried out as high throughput assay.

Traditionally, nucleotide polymerase activity assays are based on radioactivity and involve for example incorporation of radio-isotope labeled nucleoside triphosphates into the product of the polymerases. Alternative principles are used in biochemical and cell-based approaches but involve technical limitations. Known biochemical methods based on the incorporation of labeled nucleotides are heterogeneous and involve multiple washing steps. Furthermore, the incorporation of fluorescent nucleotide analogs involves the risk of artifacts due to interaction of the dyes used within the active enzymatic pocket, which clearly lower signal intensities. Cell-based methods such as qRT-PCR are based on temperature profiles and expensive components. In addition the throughput is limited. Classical reporter gene assays require lengthy preparation (such as molecular cloning in regard to each tested compound) and optimization for each tested compound.

WO 2012/024639 discloses a FRET based assay for detecting nucleotide polymerase activity. The assay of WO 2012/024639 includes fluorophore labeled template and optionally a fluorophore labeled primer and is based on the principle that a single-stranded region is flexible and allows two fluorophores or a fluorophore and a quencher to come into close proximity. FIG. 1 of WO 2012/024639 shows the so-called primer-template duplex. The primer and the template are covalently coupled and have a stem-loop structure. This duplex comprises a double stranded region acting as a primer and a single stranded region acting as a template for the polymerase. At the 5' end of the template a first FRET label is attached and at the 2' end of the template or in the primer region a second FRET label is attached. Before addition of a polymerase the single stranded template is rather flexible and proximity of both FRET labels is possible. After polymerization of a second strand the template loses its flexibility and the FRET labels cannot come in close proximity. This activity of the polymerase results in a decrease in FRET. Thus, the assay is restricted to templates ensured not to build secondary structure such as stamp formation. Furthermore, the assay described is based on qPCR and requires different temperatures during different steps. Therefore, a thermal cycler is essential.

Kits disclosed by WO 2012/024639 comprises a polymerase and a primer-template duplex. Said duplex may consist of a primer and a template which may be added separately to the reaction mixture for detection of the polymerase activity. In such a case both may be labeled. In addition the kit comprises nucleoside triphosphates. Nevertheless, these kits do not contain three different oligonucleotides, two acting as a probe and being not able to build a duplex and a third oligonucleotide acting as an initiator.

So far, no homogeneous method for determining the activity of nucleotide polymerases at ambient temperatures is known. Furthermore, a valuable advantage of the inventive methods is their adaptability, which allows to develop new variants of the method very fast and easily, in particular variants of the method adapted to several polymerases.

It is the objective of the present invention to provide methods for detection of nucleotide polymerase activity and especially methods of detecting compounds that modulate nucleotide polymerase activity by detecting product formation using determination of close proximity of two sequence specific nucleotide probes which may hybridize with the polymerase product. Determination of close proximity may thereby based on proximity dependent energy transfer, such as förster resonance energy transfer, or protein fragment complementation. The present invention was found suitable to measure nucleotide polymerase product formation, by means of highly specific binding of nucleotide probes and, thus, generation of a proximity-based, time-resolved energy transfer, such as förster resonance energy transfer (TR-FRET) signal.

This novel technology facilitated for the first time the establishment of homogeneous assay formats with working volumes of <10 µL, was found to be amenable to the use of 1536-well micro titer plates, with high signal-to-background ratio and very robust assay performance and reliability (z'>0.8). The assay has been tested and used for the identification of small molecule modulators of nucleotide polymerase activity, as well as to assess selectivity of inhibitors against these enzymes sourced from different organisms and of different cellular functions, in a high-throughput format. Furthermore, the specific design of the detection method is conveniently adaptable to varying spectroscopic detection technologies and different nucleotide polymerases.

The objective of the present invention is solved by the teaching of the independent claims. Further advantageous features, aspects and details of the invention are evident from the dependent claims, the description, the figures, and the examples of the present application.

The present invention provides methods for detection of nucleotide polymerase activity comprising the following steps:

a) providing a reaction mixture comprising said polymerase, an initiator, and nucleoside triphosphates,
b) providing conditions sufficient to allow the polymerase an assembling of nucleotides,
c) stop polymerase assembling of nucleotides,
d) adding a donor nucleotide probe and an acceptor nucleotide probe wherein said donor nucleotide probe and said acceptor nucleotide probe are each conjugated to a non-radioactive label, wherein said labels allow determination of close proximity of said nucleotide probes,
e) providing conditions sufficient to allow the nucleotide probes to hybridize with the product of step b) and
f) determining if said donor and acceptor nucleotide probes are in close proximity wherein close proximity correlates with the activity of the nucleotide polymerase.

In general the present invention refers to methods for detection of nucleotide polymerase activity in a sample or reaction mixture by using two sequence specific oligonucleotides as probes, a donor and an acceptor nucleotide probe. The sequences of these probes are chosen to allow hybridization with the product of the nucleotide polymerase to be tested. Thereby hybridization of said probes takes place in close proximity to one another. Additionally, the probes are labeled. The labels of a donor and an acceptor nucleotide probe allow determination of hybridization to the product because these labels generate a signal when being in close proximity. The signal generated, such as fluorescence or luminescence, can be determined.

In a preferred embodiment, the present invention refers to methods for detection of nucleotide polymerase activity in a sample or reaction mixture using the principle of protein fragment complementation. A reporter protein is split into two parts, which are inactive but are known to reconstitute function of the protein by non-covalent binding when being in close proximity. Thus one embodiment of the present invention is a method based on the association of inactive reporter protein fragments that are used as labels of the donor and acceptor nucleotide probes. Thereby "inactive" means that each fragment of the reporter protein alone shows not the function of the protein to be determined such as enzyme activity or fluorescence.

One preferred embodiment of the present invention is a method for detection of nucleotide polymerase activity comprising the following steps:

a) providing a reaction mixture comprising said polymerase, an initiator, and nucleoside triphosphates,
b) providing conditions sufficient to allow the polymerase an assembling of nucleotides,
c) stop polymerase assembling of nucleotides,
d) adding a donor nucleotide probe and an acceptor nucleotide probe wherein said donor nucleotide probe is conjugated to a first fragment of a reporter protein and the acceptor nucleotide probe is conjugated to a second fragment of said reporter protein wherein these fragments are able to associate and to restore function of the reporter protein in case of close proximity of said nucleotide probes,
e) providing conditions sufficient to allow the nucleotide probes to hybridize with the product of step b) and
f) determining if said donor and acceptor nucleotide probes are in close proximity wherein close proximity correlates with the activity of the nucleotide polymerase.

Therefore the present invention refers to methods or detection of nucleotide polymerase activity, wherein determining if said donor and acceptor nucleotide probes are in close proximity is performed by measuring function or activity of the reporter protein, such as emission of light in particular of luminescence or fluorescence, preferably by colorimetric analyses.

Any reporter protein that can be split into two parts or domains and reconstituted non-covalently may be used as labels in the inventive methods. The two parts or labels just have to be brought together by the donor and acceptor nucleotide probe upon hybridization to the polymerase product allowing the reporter protein to reconstitute in its native three-dimensional structure, which produces a detectable readout.

Suitable as reporter proteins are bioluminescent reporter and fluorescent reporter. The term "bioluminescent reporter" as used herein refers to any kind of oxidative enzyme creating chemiluminescence or bioluminescence when interacting with a luminogenic substrate. The bioluminescent reporter needs mostly an overlap of 10-30 amino acids of the parts or domains. Only this overlap allows interaction of these proteins restoring enzymatic function. Preferably, the bioluminescent reporter is selected from the group comprising or consisting of: beetle luciferases (including firefly luciferase), *Renilla*-luciferin 2-monooxygenase (also called *Renilla*-type luciferase), color variants of firefly luciferase and aequorin. In particularly preferred embodiments the bioluminescent reporter is firefly luciferase from the firefly *Photinus pyralis*.

When using firefly luciferase, one label consist of the C-terminal domain of the firefly luciferase, preferably of 153 amino acids from amino acid 397 to 550 and the second label consists of the N-terminal domain of the firefly luciferase, particularly preferred the first 416 amino acids from firefly luciferase (amino acids 1-416). It is preferred that the N- and C-terminal firefly luciferase domains have an overlap of 15-25 amino acids, even more preferably of 17-21 amino acids and particularly preferred of 19 amino acids, and most preferably of the amino acids 397-416 of the firefly luciferase. Such an overlap seems to be necessary for the luciferase activity once reconstituted as a result of both parts having come into close proximity.

Determining whether the donor and acceptor nucleotide probes are in close proximity may be done by measurement of luminescence of the firefly luciferase wherein occurrence of luminescence indicates hybridization of the donor and acceptor nucleotide probes and correlates with the activity of the nucleotide polymerase.

When using luciferase as a reporter protein, step f) comprises preferably adding a luciferin substrate, such as luciferin, to the reaction mixture or to the host cell prior to determination. The total amount of light emitted from bioluminescence is typically small and not detectable by the human eye, but it can normally detected using a photodetector as part of a luminescence spectrometer or by using a sensitive CCD camera Luciferins, such as D-Luciferin ($LH_2$), are a class of small-molecule substrates that are oxidized in the presence of bioluminescent reporter to produce oxyluciferin and energy in the form of light that can be detected. The firefly luciferase catalyzes the following chemical reaction:

Adenylation of a substrate, such as luciferin, using ATP and

Oxidation of the resulting luciferyl adenylate.

Light is emitted because the reaction forms oxyluciferin in an electronically excited state. Thus, light is emitted when luciferase acts on the appropriate luciferin substrate.

The term "fluorescent reporter" as used herein refers to a fluorescent protein that absorbs light energy of a specific wavelength and re-emits light at a longer wavelength. Preferred herein are fluorescent proteins, such as GFP (green fluorescent protein), YFP (yellow fluorescent protein) and DsRed (red fluorescent protein), which can be attached to the oligonucleotide forming the nucleotide probes.

Bringing the fragments within proximity by hybridization of the probes to the polymerase product, allows the reporter protein to associate and emit its fluorescent signal. This fluorescent signal can be detected. In addition, the intensity of the fluorescence emitted is proportional to the activity of the nucleotide polymerase.

In another preferred embodiment, the present invention refers to methods for detection of nucleotide polymerase activity in a sample or reaction mixture using the principle of proximity dependent energy transfer, such as förster resonance energy transfer (FRET). A donor molecule, initially in its electronic excited state, may transfer energy to an acceptor molecule. Therefore the present invention refers to methods or detection of nucleotide polymerase activity, wherein the label of the donor nucleotide probe and the label of the acceptor nucleotide probe allow energy transfer which can be determined in step f).

One preferred embodiment of the present invention is a method for detection of nucleotide polymerase activity comprising the following steps:
a) providing a reaction mixture comprising said polymerase, an initiator, and nucleoside triphosphates,
b) providing conditions sufficient to allow the polymerase an assembling of nucleotides,
c) stop polymerase assembling of nucleotides,
d) adding a donor nucleotide probe and an acceptor nucleotide probe wherein said donor nucleotide probe and said acceptor nucleotide probe are each conjugated to a non-radioactive label, wherein said labels allow energy transfer in case of close proximity of said nucleotide probes,
e) providing conditions sufficient to allow the nucleotide probes to hybridize with the product of step b) and
f) determining energy transfer between said labels of the nucleotide probes by spectroscopic technique, wherein energy transfer correlates with the activity of the nucleotide polymerase.

One detection principle suitable for the methods of the present invention and particular for determining energy transfer between said labels of the nucleotide probes by spectroscopic technique, is called amplified luminescent proximity homogeneous assay (Alpha) technology, which is a bead-based detection mode which also measures the interaction of two molecules bioconjucated to donor and acceptor beads. When excited at 680 nm, the donor bead produces singlet oxygen. If the acceptor bead is within a 200 nm distance, the singlet oxygen transfers energy (chemical energy) to the donor resulting in production of light of specific wavelength (luminescence). The amount of produced light is directly proportionate to the amount of bound donor-acceptor beads.

Thus, the present invention provides further methods for detection of nucleotide polymerase activity comprising the following steps:
a) providing a reaction mixture comprising said polymerase, an initiator, and nucleoside triphosphates,
b) providing conditions sufficient to allow the polymerase assembling of nucleotides,
c) stop polymerase assembling of nucleotides,
d) adding a donor nucleotide probe and an acceptor nucleotide probe wherein the donor nucleotide probe is conjugated to a donor bead for amplified luminescent proximity homogenous assay and the acceptor nucleotide probe is conjugated to an acceptor bead for amplified luminescent proximity homogenous assay,
e) providing conditions sufficient to allow the nucleotide probes to hybridize with the product of step b) and
f) determining luminescence of the acceptor bead wherein said luminescence correlates with the activity of the nucleotide polymerase.

Beads for amplified luminescent proximity homogenous assay are latex-based and coated with a layer of hydrogel that minimizes non-specific binding and self-aggregation. They are approximately 250 nm in diameter. They are too small to sediment in biological buffers, yet they are large enough to be centrifuged and/or filtered following bioconjugation. Donor beads contain a photosensitizer, such as phthalocyanine, which converts ambient oxygen to an excited form of $O_2$, singlet oxygen upon illumination at 680 nm. Acceptor beads contain aromatic structures such as thioxene, anthracene, and rubrene, capable of absorbing singlet oxygen and emitting light. Donor and acceptor beads for amplified luminescent proximity homogenous assay are marketed by PerkinElmer. They are available bound to streptavidin or antibodies, such as anti-digoxygenin. Furthermore, one can also purchase customer labeled beads, for example bound to nucleotides or functionalized to bind nucleotides in simple chemical reactions.

Within its 4 μsec half-life, singlet oxygen can diffuse approximately 200 nm in solution. If an acceptor bead is within that proximity, energy is transferred from the singlet oxygen to the acceptor bead, subsequently culminating in light production at a specific wavelength, such as 520-620 nm or 615 nm. In the absence of an acceptor bead, singlet oxygen falls to ground state and no signal is produced.

Another detection principle suitable for the methods of the present invention is FRET, a mechanism describing energy transfer between two light-sensitive molecules (chromophores). Measurements of FRET efficiency can be used to determine if two chromophores, such as fluorophores, are within a certain distance of each other. FRET is a dynamic quenching mechanism because energy transfer occurs while the donor is in the excited state.

Thus, the present invention provides methods for detection of nucleotide polymerase activity comprising the following steps:
a) providing a reaction mixture comprising said polymerase, an initiator, and nucleoside triphosphates, b) providing conditions sufficient to allow the polymerase assembling of nucleotides, c) stop polymerase assembling of nucleotides, d) adding a donor nucleotide probe and an acceptor nucleotide probe wherein the donor nucleotide probe is conjugated to a fluorophore being a donor for förster resonance energy transfer and the acceptor nucleotide probe is conjugated to a fluorophore being a fluorescence quencher or an appropriate acceptor for förster resonance energy transfer, e) providing conditions sufficient to allow the nucleotide probes to hybridize with the product of step b) and f) determining fluorescence wherein said fluorescence correlates with the activity of the nucleotide polymerase.

Within the inventive methods two sequence specific oligonucleotides are used as probes, which hybridize with the product of the nucleotide polymerase. These oligonucleotides or probes hybridize in near proximity, which means with distance of only a few bases or nucleotides (preferably 2-3 bases). Furthermore, these probes are each conjugated to a label such as protein fragments, beads for Alpha technology, a fluorophore, or a quencher coming in close proximity upon hybridization of the probes with the product (see FIGS. 1 and 2). These labels are selected to allow determination of close proximity, for example by determination of energy transfer, after hybridization of both probes. Therefore, more product formation by the nucleotide polymerase correlates with a more intensive signal of the acceptor nucleotide probe, a decrease in the signal of the donor nucleotide probe or a increase in signal of the protein reformed from protein fragments coupled to acceptor and donor nucleotide probe.

The term "initiator" as used herein refers i.a. to an oligonucleotide acting as a template for formation of a complementary oligonucleotide by a nucleotide polymerase or as a primer for a template-independent nucleotide polymerase covalently coupling nucleotides to said primer. Thus, the term "initiator" as used herein comprises templates and primers. As used herein, the term "primer" refers to a provided oligonucleotide that is extended by covalent bonding of nucleotide monomers or to oligonucleotides providing a pre-existing 3'-OH group the polymerase may add nucleotides onto. The initiator may be a single-stranded oligonucleotide or a double-stranded oligonucleotide or may contain regions being single-stranded as well as regions being double-stranded (such as a molecule having a single-strand 3' overhang of the double-strand region).

The inventive methods are suitable for detection of activity of several polymerases. The choice of an appropriate template depends mainly from the polymerase to be tested. A person skilled in the art knows how to find a template appropriate for a specific polymerase. Thus, a template may be a part of a gene, especially the promoter region, normally transcribed by the specific polymerase.

The activity of DNA and RNA polymerases may be measured. One embodiment of the present invention refers to methods, wherein the nucleotide polymerase is selected from the group comprising or consisting of DNA dependent DNA polymerase, RNA dependent DNA polymerase, DNA dependent RNA polymerase, RNA dependent RNA polymerase, independent RNA polymerase, and independent DNA polymerase.

Within the present invention it is preferred that the nucleotide polymerase is selected from the group comprising or consisting of T7 RNA polymerase (such as bacteriophage T7 RNA polymerase), E. coli RNA polymerase, mitochondrial RNA-Polymerase (such as POLRMT), mitochondrial DNA-Polymerase, bacterial RNA polymerases (RNAPs), viral DNA polymerases, HCV RNA-dependent RNA polymerase, T3 RNA polymerase, human DNA-directed RNA polymerase II, RNA-dependent DNA polymerase, and terminal deoxynucleotidyl transferase (TdT).

A suitable template for a T7 RNA polymerase and E. coli RNA polymerase is shown by Seq ID No. 3 and 4. Seq ID No. 5 is an example of an initiator suitable for a method for detection of human mitochondrial DNA-Polymerase activity. Activity of human mitochondrial RNA-Polymerase may be tested using the mitochondrial light-strand promoter as DNA-template (mitochondrial genome bp 1-477) as an initiator, which is shown by SEQ ID No.1. For testing the activity of mouse mitochondrial RNA-polymerase a suitable DNA transcription template corresponds to the murine mitochondrial light-strand promoter (mLSP), as shown in Seq ID No. 2.

The term "nucleoside triphosphates" as used herein refers to a combination of one or more ribonucleotide triphosphates (GTP, UTP, CTP and ATP or nucleotide analogs thereof; rNTPs), or to deoxyribonucleic triphosphates (dGTP, dUTP, dCTP and dATP or nucleotide analogs thereof; dNTPs). Nucleoside triphosphate as mixes containing premixed dATP, dCTP, dGTP and dTTP or premixed GTP, UTP, CTP and ATP, or individually are commercially available in aqueous solutions.

As used herein, the terms "hybridization" and "hybridizing" refer to the pairing of two complementary single-stranded nucleic acid molecules (RNA/RNA, RNA/DNA or DNA/DNA) resulting in a double-stranded molecule. Base pairs are typically formed by hydrogen bonds between nucleotide units in antiparallel polynucleotide molecules or regions. Complementary polynucleotide strands or regions can base pair in the Watson-Crick manner (e.g., A to T, A to U, C to G). As used herein, two nucleic acid molecules may be hybridized, even if the base pairing is not completely complementary. Accordingly, mismatched bases do not prevent hybridization of two nucleic acid molecules provided that appropriate conditions, well known in the art, are used.

Step a) of the inventive methods refers to "providing a reaction mixture comprising a polymerase, an initiator, and nucleoside triphosphates". Step a) of the inventive method could also be defined as mixing a polymerase, an initiator, and nucleoside triphosphates. Step a) as well as the complete method of the invention could be performed in solution. This means that the polymerase, the initiator, nucleoside triphosphates and optionally further components such as a candidate substance may be dissolved together in one solution or that a solution of the polymerase is mixed with a solution containing an initiator and a solution containing nucleoside triphosphates. A reaction mixture of the inventive method has to include at least a polymerase, the initiator and nucleoside triphosphates.

The provided or created reaction mixture could be based on any suitable solvent as well as buffer solutions or a mixture of a solvent, especially an organic solvent and a buffer. Preferably all components are added to an appropriate buffer. A solvent used for the components of the methods, in particular of the candidate substance should not interfere with another component of the inventive method. Denaturation of the enzyme should be avoided, too. Hence denaturants, surfactants or other amphiphilic molecules in the reaction mixture should be avoided.

Furthermore a suitable reaction mixture should not have own fluorescence or bioluminescence. Suitable are reaction mixtures on basis of Tris- and triethanolamine buffers. The buffer regulates the pH of the reaction, which affects the DNA polymerase activity and stability. It is preferred that the pH-value of the used buffer is around the optimum pH value for the used polymerase, which is commonly about pH 8. Therefore it is preferred that the used buffer has a pH between 7.5 and 8.5. Suitable buffers should not contain or only contain minor amounts of Fluorescence quenching substances such as DMSO, iodine ions, and glycine.

When the detection principle of the inventive method is based on Alpha technology the use of the following transition metal ions: $Al^{3+}$, $Fe^{2+}$, $Fe^{3+}$, $Cu^{2+}$, $Ni^{2+}$ and $Zn^{2+}$ should be avoided. These metals have been shown to be potent singlet oxygen quenchers in the mM and sub-mM ranges.

Inner filters should also be avoided, which are compounds that will absorb light, in particular light at the excitation wavelength of the donor fluorophore or the donor bead, or light at the emission wavelength of the donor fluorophore, the acceptor fluorophore or the acceptor bead.

Other mechanisms to be avoided, in particular when the detection principle of the inventive method is based on Alpha technology, are compounds that act as donor or acceptor analogs. Donor analogs are structures capable of generating singlet oxygen.

These are usually aromatic structures such as porphyrins. Acceptor analogs are compounds capable of absorbing singlet oxygen. These are usually aromatic heterocyclic compounds. In case the candidate substance to be tested is such an analog it is preferred to use another detection principle such as FRET or protein fragment complementation.

The reaction mixture may include purified or unpurified nucleotide polymerases from viruses, bacteria, fungi, archaea, eukaryotic cells or tissues. The polymerase is optionally naturally occurring, or artificially (e.g., recombinantly) produced. Thereby, the inventive method may be used to analyze the activity of a polymerase together with factors from a specific cell population. Thus, in regard to the present invention crude cell extracts (crude cell lysate), a subfraction of a cell lysate, a nuclear extract or a solution resulting from total protein extraction or purified polymerase can be used as basis for a reaction mixture or may be a component of the reaction mixture.

As used herein a crude cell extract results from disruption of cells and removal of cellular debris generated by cell lysis. The extract will contain a complex mixture of all proteins from the cell cytoplasm, and some additional macromolecules, cofactors and nutrients.

Thereby it is preferred to use a nuclear extract resulting from lysed cells. Kits for preparation of nuclear extracts are commercially available (for example Nuclei EZ Prep of Sigma Aldrich). Nuclear extract can also be prepared according to the method of Schreiber et al (Schreiber et al., 1990), In fact, it depends on the problem to be solved by the assay whether an in vitro assay based on purified polymerase, on nuclear extract or on crude cell extract is preferred.

A preferred embodiment of the present invention refers to methods for detection of nucleotide polymerase activity, wherein the reaction mixture comprises further a candidate substance to test its effect on the nucleotide polymerase activity. This candidate substance is preferably added to the reaction mixture before start of the enzymatic reaction. Alternatively the candidate substance may be preincubated with the nucleotide polymerase and added thereafter to the reaction mixture together with the nucleotide polymerase.

Enzymatic reactions start only after adding all essential components for the reaction, such as the enzyme and the substrate and when the conditions such as pH and temperature are suitable. Thus, the enzymatic reaction of the nucleotide polymerase may be started by addition of a last essential component for the reaction (for example dNTPs or the nucleotide polymerase) or by changing the conditions such as temperature or pH.

The aim of the methods for detection of nucleotide polymerase activity, wherein the reaction mixture comprises further a candidate substance is to find candidate substances having at least one biological or pharmaceutical effect on the activity of a specific nucleotide polymerase. Thus, candidate substances are examined to search for inhibitors or for activators. As mentioned before inhibitors of a specific nucleotide polymerase are promising candidates for drug development.

The candidate substance to be tested within a method of the invention for detection of nucleotide polymerase activity may be any type of chemical molecule. The method may serve to search for an inhibitor or an activator of polymerase activity depending on the problem to be solved. Isolation and characterization of substances with the potential to modulate polymerase activity may be of interest for development of a therapeutically active agent and in molecular technologies. The method of the present invention is suitable for screening large compound libraries for substances modulating polymerase activity.

In a preferred embodiment of the methods according to the invention the candidate substance can be:
  i) a small molecule,
  ii) an aptamer,
  iii) a peptide, a protein, or a protein complex,
  iv) or an antibody.

The term small molecule refers to a low molecular weight organic compound, which is by definition not a polymer. In the field of pharmacology, it is usually restricted to a molecule that also binds with high affinity to biopolymers such as proteins, nucleic acids or polysaccharides. Small molecules are broadly used as enzyme inhibitors and may be a nucleotide analog.

Aptamers are oligonucleic acid (DNA or RNA aptamers) or peptide molecules (peptide aptamers) that bind to a specific target molecule. Aptamers can be used for therapeutic purposes as macromolecular drugs. Aptamers can be created by selection from a large random sequence pool.

Antibodies are vertebrate proteins that bind very specifically to antigens. They can be formed for virtually any structure and are thus valuable tools for direct interaction with certain molecules. Recombinant techniques can be used to generate antibodies and antibody fragments that basically consist of the binding moieties of the antibodies.

Preferably the candidate substance is in solid form or a solution of the candidate substance is added. Thereby it is preferred that different concentrations of the candidate substance will be added in a way that a concentration series is formed. The evaluation of a concentration series may allow calculating the affinity of the candidate substance for binding to the polymerase. Depending on the binding affinity it may be useful to determine an optimal concentration range for the assay in advance. One embodiment of the present invention refers to a method wherein different concentrations of the candidate substance are added to reaction mixture (each concentration to one sample containing all other components of the method), which allows a quantitative determination after data analysis. $IC_{50}$ and $K_i$ values for candidate substances that inhibit polymerase activity can be determined, too.

Further embodiments of the present invention are methods for detection of nucleotide polymerase activity, wherein the reaction mixture of step a) or 1) comprises further at least one transcription or replication factor. The reaction can also include a co-factor of the nucleotide polymerase.

The terms "transcription factors" or "replication factors" as used herein refer to proteins that affect polymerase function. A transcription factor may recognize and bind to specific nucleotide sequences (usually recognition motifs of 6-8 bases), thereby controlling transcription of genetic information from DNA to messenger RNA. Transcription factors perform this function alone or with other proteins in a complex, by controlling (positively or negatively) the recruitment of the nucleotide polymerase. Transcription factors are preferably added to the reaction mixture as isolated proteins but may also be added as part of a crude cell extract or a crude nuclear extract. Replication factors are polymerase accessory proteins, which assist in polymerase recruitment and binding to polynucleic acids. A replication factor may therefore bind and subsequently stabilizes single-stranded DNA intermediates and thus prevents complementary DNA from reannealing or interact with and/or modify the activities of other proteins. In vivo, replication factors play a role in several cellular processes including replication, recombination and repair of DNA.

Preferably the reaction mixture of step a) or 1) comprises at least one transcription or replication factor influencing the nucleotide polymerase the activity is to be determined and at least one Co-factor of said polymerase.

The term "Co-factor" as used herein refers to a non-protein chemical compound that is required for the polymerase synthetic activity. Cofactors can be considered "helper molecules" that assist enzymes in catalyzing biologically reactions. A cofactor can be an inorganic ion, or a complex organic or metalloorganic molecule called a coenzyme. Metal ions are common cofactors of nucleotide polymerases. Nucleotide polymerase uses often a magnesium ion as co-factor but also cobalt ions, manganese ions, calcium ions may be co-factors of nucleotide polymerases.

A particularly preferred embodiment of the present invention refers to methods for detection of mitochondrial RNA polymerase activity, wherein the reaction mixture comprises further the mitochondrial transcription elongation factor, TEFM. TEFM has a dramatic stimulatory effect on transcription elongation in the method of the present invention. It is a factor that, on its own, can greatly stimulates POLRMT-dependent transcription and, therefore, improves the inventive method. This results in results being more sensitive and specific, in particular when identifying modulators of the enzyme activity. This factor is preferably added to the reaction mixture (step a)) before start of the enzymatic reaction. Alternatively it may be preincubated with the nucleotide polymerase and added thereafter to the reaction mixture together with the nucleotide polymerase.

The inventors optimized the inventive method in order to carry out the invention in a miniaturized 1536 well format, which does not allow mixing the reaction mixture using a shaker. Thereby, it was found that sequentially preparation of the reaction mixture is favorable. Therefore, one preferred embodiment of the present invention refers to methods wherein the provision of a reaction mixture of step a) comprises the following:

1) contacting said polymerase with an initiator, at least one transcription factor and an appropriate co-factor of the nucleotide polymerase resulting in a first reaction mixture,
2) incubating said first reaction mixture,
3) adding to said first reaction mixture the candidate substance resulting in a second reaction mixture,
4) incubating said second reaction mixture, and
5) adding to said second reaction mixture nucleoside triphosphates.

One preferred embodiment of the present invention refers to methods for detection of nucleotide polymerase activity comprising the following steps:

i) contacting said polymerase with an initiator, at least one transcription factor and an appropriate co-factor of the nucleotide polymerase resulting in a first reaction mixture,
ii) incubating said first reaction mixture
iii) adding to said first reaction mixture the candidate substance resulting in a second reaction mixture
iv) incubating said second reaction mixture
v) adding to said second reaction mixture nucleoside triphosphates,
vi) providing conditions sufficient to allow the polymerase an assembling of nucleotides,
vii) stop polymerase assembling of nucleotides,
viii) adding a donor nucleotide probe and an acceptor nucleotide probe wherein said donor nucleotide probe and said acceptor nucleotide probe are each conjugated to a non-radioactive label, wherein said labels allow determination of close proximity of said nucleotide probes,
ix) providing conditions sufficient to allow the nucleotide probes to hybridize with the product of step b) and
x) determining by spectroscopic techniques if said donor and acceptor nucleotide probes are in close proximity wherein close proximity correlates with the activity of the nucleotide polymerase.

Another preferred embodiment of the present invention refers to methods for detection of nucleotide polymerase activity comprising the following steps:

a) contacting said polymerase with an initiator, at least one transcription factor and an appropriate co-factor of the nucleotide polymerase resulting in a first reaction mixture
    incubating said first reaction mixture
    adding to said first reaction mixture the candidate substance resulting in a second reaction mixture
    incubating said second reaction mixture
    adding to said second reaction mixture nucleoside triphosphates,
b) providing conditions sufficient to allow the polymerase assembling of nucleotides,
c) stop polymerase assembling of nucleotides,
d) adding a donor nucleotide probe and an acceptor nucleotide probe wherein the donor nucleotide probe is conjugated to a fluorophore being a donor for förster resonance energy transfer and the acceptor nucleotide probe is conjugated to a fluorophore being a fluorescence quencher or an appropriate acceptor for förster resonance energy transfer,
e) providing conditions sufficient to allow the nucleotide probes to hybridize with the product of step b) and
f) determining fluorescence wherein said fluorescence correlates with the activity of the nucleotide polymerase.

Step b) of the inventive methods reads: "providing conditions sufficient to allow the polymerase assembling of nucleotides". Assembling of nucleotide refers to the polymeric activity of nucleotide polymerases wherein nucleotide molecules are synthesized by linking building blocks, namely nucleotides (the covalent binding of a 5'-phosphate to the 3'-hydroxyl group of another nucleotide, to form a phosphodiester bond). The term "sufficient conditions" refers mostly to a suitable temperature, which should not be higher than 70° C., depends on the polymerase to be tested, and is preferably room temperature (20-28° C.). "Sufficient conditions" comprise further a suitable solvent or buffer used in the reaction mixture and means further that the reaction mixture is incubated for some time, preferably between 10 minutes and 24 hours, more preferred between 20 minutes and 16 hours, further preferred between 30 minutes and 8 hours and most preferred between 1 hour and 4 hours.

Step c) of the inventive methods refers to stop of the polymerase activity, namely the assembling of nucleotides. One possibility to stop the enzymatic reaction of the polymerase is to denaturize the polymerase by heating, for example to 75° C. for 10 minutes. Alternatively, one may stop the enzymatic reaction by chelating a co-factor essential to the reaction of the tested polymerase, such as by adding EDTA. This may simply be done by adding to the reaction the nucleotide probes solved in a buffer containing a chelator.

Therefore, methods wherein step c) and step d) are carried out simultaneously are preferred within the present invention.

Step d) of the inventive methods refer to adding a donor nucleotide probe and an acceptor nucleotide probe wherein said donor nucleotide probe and said acceptor nucleotide probe are each conjugated to a non-radioactive label, wherein said labels allow determination of close proximity of said nucleotide probes.

Both nucleotide probes are preferably based on oligonucleotides having a length of 14-50 bp, more preferably a length of 16-30 bp, more preferably a length of 18-26 bp and even more preferred of 20-22 bp. The sequences of these oligonucleotides shall be chosen to be complementary to the product of the nucleotide polymerase that's activity is to be determined and shall enable the probes to hybridize with said product of the nucleotide polymerase in close spatial proximity. It is preferred that the donor nucleotide probe and the acceptor nucleotide probe hybridize to the product with not more than 4, preferred not more than 3 bases distance. But an overlap should be avoided.

The donor nucleotide probe and the acceptor nucleotide probe are functionalized by conjugation to a label, wherein said labels allow determination of close proximity of said nucleotide probes. Therefore, one nucleotide probe should be functionalized at its 5' end and the other nucleotide probe at its 3' end, so that both labels such as the fluorophores or the protein fragments are added at the ends of the nucleotide probes being in immediate vicinity after hybridization. The donor nucleotide probe and the acceptor nucleotide probe may also be functionalized by conjugation to more than one label, preferably to two labels, wherein said labels are preferably identical but are conjugated to different nucleotides of the oligonucleotide.

One aspect of the invention refers to donor nucleotide probe and the acceptor nucleotide probe functionalized by conjugation to protein fragments so that a functional protein is formed when the fragments used as labels come into close spatial proximity after hybridization of the donor and the acceptor nucleotide probe. Another aspect of the invention refers to donor nucleotide probe and the acceptor nucleotide probe functionalized by conjugation to donor and acceptor beads for amplified luminescence proximity homogenous assay, respectively. In this case the labels are chosen so that in consequence of hybridization of both nucleotide probes diffusion of singulet oxygen from donor to acceptor bead is possible.

It is preferred that the donor nucleotide probe is functionalized by conjugation to a fluorophore and the acceptor nucleotide probe is functionalized by conjugation to a quencher. It is further preferred that the donor nucleotide probe and the acceptor nucleotide probe are functionalized in a way that allows förster resonance energy transfer to occur if appropriate excitation of the fluorescent donor is given and if simultaneous binding of both probes takes place so that both fluorophores used as labels come into close spatial proximity.

Step d) of preferred inventive methods refer to addition of a donor nucleotide probe and an acceptor nucleotide probe wherein the donor nucleotide probe is conjugated to a fluorophore being a donor for förster resonance energy transfer and the acceptor nucleotide probe is conjugated to a fluorophore being a fluorescence quencher or an appropriate acceptor for förster resonance energy transfer.

The donor nucleotide probe and the acceptor nucleotide probe are functionalized by conjugation to a fluorophore or the donor nucleotide probe is functionalized by conjugation to a fluorophore and the acceptor nucleotide probe is functionalized by conjugation to a quencher. It is preferred that the donor nucleotide probe and the acceptor nucleotide probe are functionalized in a way that allows förster resonance energy transfer to occur if appropriate excitation of the fluorescent donor is given and if simultaneous binding of both probes takes place so that both fluorophores used as functional groups come into close spatial proximity. Therefore one nucleotide probe should be functionalized at its 5' end and the other nucleotide probe at its 3' end, so that both fluorophores or the fluorophore and the quencher are added at the ends of the nucleotide probes being in immediate vicinity after hybridization.

As used herein the term "fluorophore" refers to a molecule, label or moiety that is able to absorb energy from light, to transfer this energy internally and emit said energy as light having a specific range of wavelength.

As used herein the term "quencher" refers to a molecule, label or moiety that is a dark quencher, which absorbs excitation energy from a fluorophore and dissipates the energy given off via molecular vibrations (heat). This heat is thereby too small to affect the temperature of the solution.

The fluorophores used should be a pair of molecules that interact in such a manner that FRET occurs, hence can be used in fluorescence resonance energy transfer (FRET) applications as donors and acceptors of fluorescence and is also referred to as a donor-acceptor pair. Alternatively the quencher conjugated to the acceptor nucleotide probe should be able to quench the fluorescence of the fluorophore at the donor nucleotide probe.

Numerous donor-acceptor pairs are described in literature. In general, two fluorophores are a suitable donor-acceptor pair appropriate for förster resonance energy transfer if the fluorescence emission spectrum of the donor fluorophore overlaps the absorption or excitation spectrum of the acceptor fluorophore. In addition, the fluorescence lifetime of the donor fluorophore must be of sufficient duration to allow FRET to occur.

One aspect of the present invention refers to methods, wherein the fluorophore or quencher coupled to the acceptor nucleotide probe is selected from the group consisting of ATTO 647N, ATTO 612Q, Alexa Fluor® 647, Cy® 5, XL 665, BHQ-3, Chromeo™ 494, ATTO647, Alexa Fluor® 647N, ATTO 490LS, dimethylaminoazobenzenesulfonic acid (CAS 547-58-0), QXL™ 610, QXL™ 670, QXL™ 680, Iowa Black® RQ, IRDye® QC-1, QSY® 21, DDQ-II™, LCred™, Quasar® 670, and Oyster®-645 and wherein the fluorophore coupled to the donor nucleotide probe is a chelate or a cryptate bound lanthanide.

XL665 is a phycobilliprotein pigment purified from red algae and is a large heterohexameric edifice of 105 kDa, cross-linked after isolation. The term "chelate or a cryptate bound lanthanide" refers to a complex between a cationic lanthanide and a cryptand. Cryptands are a family of synthetic bi- and polycyclic multidentate ligands or three-dimensional analogues of crown ethers for cations. The 3-dimensional interior cavity of a cryptand provides a binding site for "guest" ions such as lanthanides. The most common and most important cryptand is $N[CH_2CH_2OCH_2CH_2OCH_2CH_2]_3N$ or 1,10-diaza-4,7,13,16,21,24-hexaoxabicyclo[8.8.8]hexacosane. Many cryptands are commercially available under the tradename "Kryptofix."

Preferred herein are cryptates of europium ($Eu^{3+}$) and terbium ($Tb^{3+}$) whereby the cryptates of europium ($Eu^{3+}$) are particularly preferred. Especially europium cryptate fluorophores were shown to be very advantageous with respect to the present invention, as said fluorophores have a characteristic luminescence spectrum which can be very well separated from the possible fluorescence of other components. The europium cryptate fluorophore is preferably excited at a wavelength of 320 nm. Emission is measured at 620 nm. Fluorescence of the europium cryptate fluorophores and terbium cryptate fluorophores is significantly longer compared to that of other fluorophores, so that the fluorescence of the europium cryptate fluorophores or respectively terbium cryptate fluorophores can be well and accurately determined despite a possible background fluorescence caused by other components or other fluorophores, such as the donor fluorophore.

The term "conjugated to a label" as used herein refers to non-covalent interaction and to covalent coupling of a nucleotide probe or the oligonucleotides the nucleotide probe is based on to a label, such as a fluorophore. Covalent coupling or binding refers to a chemical bond that involves sharing of electron pairs between atoms. The chemical reactions that make possible label attachment to oligonucleotides are well characterized and facilitate the attachment of biomolecules through their common chemical groups. One coupling strategy relies on an unprotected 5' amino linker on the oligonucleotide reacting with the peptide C-terminus.

The term "non-covalent interaction" as used herein refers to conjugation mediated by a receptor and the corresponding ligand wherein one is attached by covalent bonding to the oligonucleotide of the probe and the other to the label. The term "mediated non-covalent interaction" means that the oligonucleotide of the probe is covalently coupled to a receptor or its ligand wherein the label is covalently coupled to the appropriate biding partner or ligand. The receptor binds to its ligand by non-covalent interaction, but by electromagnetic interactions between molecules. There may be ionic interaction, van der Waals forces, or hydrogen bonding. Therefore, one preferred embodiment of the invention refers to methods, wherein the donor nucleotide probe or the acceptor nucleotide probe is conjugated to a label such as a fluorophore by covalent bonding or by non-covalent interaction.

Suitable receptor/ligand systems are for example the biotin/streptavidin (respectively Avidin/NeutrAvidin) system or the system comprising an immunoglobulin and an immunoprotein binding protein such as protein G or protein A. It is also possible to use an antibody (receptor) and an antigene (ligand) such as digoxygenin and anti-digoxygenin.

The interaction of biotin and avidin or streptavidin has been exploited for use in many biologically methods. Because the biotin label is stable and small, it rarely interferes with the function of labeled molecules enabling the avidin-biotin interaction to be used for the development of robust and highly sensitive assays. It has been found that the fluorescence signal measured within the inventive method is very strong if at least one nucleotide probe is conjugated to its label, such as a fluorophore, using the biotin/streptavidin system.

One aspect of the present invention refers to methods, wherein the donor nucleotide probe or the acceptor nucleotide probe is conjugated to the label or fluorophore by non-covalent interaction mediated by biotin covalently coupled to the donor nucleotide probe or respectively the acceptor nucleotide probe and streptavidin covalently coupled to the label or the fluorophore.

Another aspect of the present invention refers to methods, wherein the donor nucleotide probe or the acceptor nucleotide probe is conjugated to the label or fluorophore by non-covalent interaction mediated by digoxygenin covalently coupled to the donor nucleotide probe or respectively the acceptor nucleotide probe and anti-digoxygenin (an antibody against digoxigenin) covalently coupled to the label or the fluorophore.

A preferred embodiment of the present invention refers to methods using a first nucleotide probe covalently coupled to ATTO647N and Europium cryptate bound to streptavidin which binds to a second nucleotide probe via biotin conjugated to said second nucleotide probe. Another preferred embodiment of the present invention refer to methods using a first nucleotide probe covalently coupled to Europium cryptate and XL665 bound to streptavidin which binds to a second nucleotide probe via biotin conjugated to said second nucleotide probe. A preferred embodiment of the present invention refers to methods using a first nucleotide probe bound to digoxygenin which binds to a donor bead for Alpha technology via anti-digoxygenin and an acceptor bead for Alpha technology bound to streptavidin which binds to a second nucleotide probe via biotin conjugated to said second nucleotide probe.

When using the biotin/streptavidin system to conjugate a nucleotide probe to a label it has been found that it is beneficial to incubate the streptavidin coupled labeled with random oligonucleotides to lock unspecific binding. Therefore, another aspect of the present invention refers to methods, wherein unspecific binding of the streptavidin covalently coupled to the label or the fluorophore is blocked using random oligonucleotides before the streptavidin covalently coupled to the label or fluorophore is conjugated to the biotin covalently coupled to the donor nucleotide probe or the acceptor nucleotide probe.

Several companies offer custom-made oligonucleotides having different purification options, various synthesis scales and with different modifications, such as biotinylation or coupling to fluorophores, suitable for use as nucleotide probes. Furthermore, various fluorophores, also fluorophores conjugated to streptavidin or biotin, are commercially available. Additionally it is possible to use commonly known chemistry to label oligonucleotides with fluorophores, or even buy ready to use kits for labeling of oligonucleotides with fluorophores (e.g. ARES™ Alexa Fluor® 647 DNA Labeling Kit of Life Technologies®).

The inventors could show that the signal strength of the measured fluorescence, namely the signal to background ratio, is optimal for equimolar concentrations of donor nucleotide probe and an acceptor nucleotide probe. Therefore, another embodiment of the present invention refers to methods for detection of nucleotide polymerase activity, wherein the donor nucleotide probe and the acceptor nucleotide probe are used in a ratio from 1:2 up to 2:1. A further preferred embodiment of the present invention refers to methods for detection of nucleotide polymerase activity, wherein the donor nucleotide probe and the acceptor nucleotide probe are used in a ratio of 1:1

Step e) of the inventive methods reads: providing conditions sufficient to allow the nucleotide probes to hybridize with the product of step b). Hybridization of nucleotide probes and the product of the nucleotide polymerase refer to the annealing of the nucleotide probes to the product, namely a polynucleotide made by the polymerase, by binding of complementary bases. The term "sufficient conditions" refers mostly to a suitable temperature, which should not be higher than 70° C. and is preferably room temperature. "Sufficient conditions" comprise further a suitable solvent or buffer used in the reaction mixture and a suitable length of this step. The length of this step depends mostly of the amount of nucleotide polymerase used and thus, the quantity of the test sample, and is preferably between 15 minutes and 30 hours, more preferred between 30 minutes and 24 hours, further preferred between 8 hours and 20 hours and most preferred over night, which shall be around 16 hours.

Further embodiments of the present invention are methods for detection of nucleotide polymerase activity, wherein the complete method is carried out at room temperature. Alternatively the inventive method or only step b) referring to the enzymatic reaction of the nucleotide polymerase may be carried out at a temperature between 20° C. and 50° C., preferably at 37° C.

Step f) of the inventive methods comprises determining if said donor and acceptor nucleotide probes are in close proximity wherein close proximity correlates with the activity of the nucleotide polymerase. Step f) may also be formulated as determining if the label of said donor nucleotide probe and the label of said acceptor nucleotide probe are in close proximity wherein close proximity correlates with the activity of the nucleotide polymerase. This is preferably done by colorimetric analyses or spectroscopy, such as fluorescence spectroscopy.

In a preferred embodiment step f) comprises determining if said donor nucleotide probe and said acceptor nucleotide probe have hybridized with the product of the nucleotide polymerase, so that the label of said donor nucleotide probe being a first inactive fragment of an reporter protein and the label of said acceptor nucleotide being a second inactive fragments of said reporter protein are able to associate and reform the active reporter protein. Consequently, determination of close proximity may be done by detection the corresponding activity of the reporter proteins such as enzyme activity or fluorescence. When determining enzyme activity step f) may comprise adding a substrate such as luciferin for luciferase. Furthermore, it is obvious that in this case step f) comprises also provision of sufficient conditions for the enzyme reaction, which means a suitable temperature, preferably room temperature (20-28° C.), if necessary a co-substrate or cofactor such as ATP-Mg2+ is provided, a suitable pH, a suitable solvent or buffer used and means further that the reaction mixture is incubated for some time, preferably around 10 to 30 minutes. In an assay using luciferase, a flash of light or bioluminescence is generated that decays rapidly after the enzyme and substrates are combined. This may be detected using multi-technology microplate readers or luminometers. In general luminescence may be detected by Photon Counting. Step f) of a preferred embodiment of the inventive method refers therefore to determining intensity of luminescence. A change in signal intensity is indicative for the amount of product made by the nucleotide polymerase. For example a decrease in luminescence indicates a decrease in activity of the nucleic polymerase and an inhibitory effect of the candidate substance.

In another preferred embodiment step f) comprises determining if said donor nucleotide probe and said acceptor nucleotide probe have hybridized with the product of the nucleotide polymerase, so that an energy transfer between the label of said donor nucleotide probe and the label of said acceptor nucleotide probe is possible. The label of the donor nucleotide probe, initially in its electronic excited state, may transfer energy to the label of the acceptor nucleotide probe.

There are several ways of measuring the efficiency of energy transfer, in general by monitoring changes in the fluorescence emitted by the label of the donor nucleotide probe or the label of the acceptor nucleotide probe. One method is to measure the variation in acceptor emission intensity. When the donor and acceptor are in close proximity due to the interaction of the two probes with the product of the polymerase, the acceptor emission will increase because of the intermolecular FRET from the donor to the acceptor. FRET can also be detected by the appearance of sensitized fluorescence of the acceptor or by quenching of donor fluorescence.

Therefore, in a preferred embodiment step f) comprises determining fluorescence, wherein said fluorescence correlates with the activity of the nucleotide polymerase. This may be done by determining the fluorescence at the emission maximum of the acceptor nucleotide probe or the donor nucleotide probe (in case of using a quencher) using photometry. The specific design of the nucleotide probes, allows using the FRET effect to determine and characterize activity of the nucleotide polymerase. Because the principle of FRET needs spatial proximity binding of the nucleotide probes to the product, the change in signal intensity by FRET is indicative for the amount of product made by the nucleotide polymerase. Step f) of the preferred embodiment of the inventive method refers therefore to determining intensity of fluorescence at a specific wavelength, namely the emission maximum of the label or fluorophore at the acceptor nucleotide probe. A decrease in fluorescence indicates a decrease in activity of the nucleic polymerase and an inhibitory effect of the candidate substance. Also the principle of fluorescence quenching needs spatial proximity binding of the nucleotide probes to the product, so that the change in signal intensity is indicative for the amount of product made by the nucleotide polymerase. Step f) of the preferred embodiment of the inventive method refers therefore further to determining fluorescence at the emission maximum of the label or fluorophore at the donor nucleotide probe if the acceptor nucleotide probe is conjugated to a quencher. In this case an increase in fluorescence indicates a decrease in activity of the nucleic polymerase and an inhibitory effect of the candidate substance.

In all cases, the method of the present invention enables the detection of nucleotide polymerase activity, with a cost-effective optical or photometrical measurement. The direct optical detection method allows further for analyzing the binding affinity and has the advantage that the method of the invention is suitable for miniaturizing and automatization.

Determining a decrease or increase in energy transfer and in resulting fluorescence requires two steps, excitation at an excitation wavelength of the label of the donor nucleotide probe or donor fluorophore which not excites or only minimally excites the label of the acceptor nucleotide probe or the acceptor fluorophore (if present) and subsequently measurement of the emission at the emission wavelength of label of the acceptor nucleotide probe or the acceptor fluorophore which is distinguishable from the emission of the donor fluorophore. Determining a decrease or increase in fluorescence may also refer to, excitation at an excitation wavelength of a fluorophore (such as a fluorescent protein reformed from inactive fragments) and subsequently measurement of the emission at the emission wavelength of said fluorophore. Determining a decrease or increase in fluorescence may also refer to excitation at an excitation wavelength of a fluorophore as label of the donor nucleotide probe and subsequently measurement of the emission at the emission wavelength of said fluorophore, which is possibly quenched by the quencher bound to the acceptor nucleotide probe. Nevertheless, also within an embodiment based on FRET it is possible to measure the alteration in donor fluorescence (emission of the donor fluorophore) instead of the alteration in acceptor fluorescence.

It is common knowledge that determining a change in a signal, such as fluorescence or luminescence decrease or increase is only possible if a blank sample and/or a sample containing a substance to be known not to modulate polymerase activity is measured, too. Therefore, step f) comprises preferably comparison of the measured signal, such as emission with a blank value and/or the value of at least one reference sample.

One aspect of the present invention refers to methods for detection of nucleotide polymerase activity, wherein the assay is adapted to be carried out as a homogenous high throughput screen. Thereby it is preferred that the method is suitable to be carried out in a 384 well assay format or even more preferred in a 1536 well assay format, which allows no mixing of the reaction mixture by a shaker.

The term "homogeneous assay" refers to an assay format allowing to carry out an assay-measurement by a simple mix and read procedure without the necessity to process samples by separation or washing steps.

For controls, to ascertain whether the method is properly working in the hands of the experimenter, a negative control sample and a positive reference sample (a sample containing a substance known to modulate nucleotide polymerase activity) should always be used together with the candidate substance to be tested. This is a standardized procedure with biologically or diagnostic assays. This means that at the same time or immediately one after the other, not only the candidate substance is tested within the inventive method, but also a negative control sample, which can be a sample without enzyme, template or NTPs, but also a blank control comprising all components except for a candidate substance.

Another embodiment of the present invention is a kit for detection of nucleotide polymerase activity comprising:
A) a donor nucleotide probe and an acceptor nucleotide probe wherein said donor nucleotide probe and said acceptor nucleotide probe are each conjugated to a non-radioactive label, allowing determination of close proximity of said nucleotide probes,
B) said polymerase,
C) an initiator appropriate for said polymerase.

The donor nucleotide probe and the acceptor nucleotide probe are preferably not able to hybridize (build a duplex) with each other or with themselves; they should both be able to bind the transcript.

The initiator of the kids of the invention is a single-stranded oligonucleotide or a double-stranded oligonucleotide or may contain regions being single-stranded as well as regions being double-stranded (such as a molecule having a single-strand 3' overhang of the double-strand region). The initiator acts as a template for formation of a complementary oligonucleotide by a nucleotide polymerase or as a primer for a template-independent nucleotide polymerase covalently coupling nucleotides to said primer. Thus, the term "initiator" as used herein comprises templates and primers. As used herein, the term "primer" refers to a provided oligonucleotide that is extended by covalent bonding of nucleotide monomers or to oligonucleotides providing a pre-existing 3'-OH group the polymerase may add nucleotides onto.

A further preferred embodiment of the present invention is a kit for detection of nucleotide polymerase activity comprising:
A) a donor nucleotide probe and an acceptor nucleotide probe wherein said donor nucleotide probe and said acceptor nucleotide probe are each conjugated to a non-radioactive label, allowing determination of close proximity of said nucleotide probes,
B) said polymerase,
C) an initiator appropriate for said polymerase, and wherein the probes of A) are not able to hybridize with each other or with themselves.

The kits of the present invention contain at least three different types of oligonucleotides, a first probe, a second probe and an initiator. Preferably these kits comprise a donor nucleotide probe conjugated to a first fragment of a reporter protein and an acceptor nucleotide probe conjugated to a second fragment of said reporter protein wherein these fragments are able to associate and to restore function of the reporter protein in case of close proximity of said nucleotide probes.

Another embodiment of the kits of the invention comprises a donor nucleotide probe and an acceptor nucleotide probe wherein the donor nucleotide probe is coupled to a donor bead for amplified luminescent proximity homogenous assay and the acceptor nucleotide probe is coupled to an acceptor bead for amplified luminescent proximity homogenous assay.

These kits comprise further preferred a donor nucleotide probe and an acceptor nucleotide probe wherein the donor nucleotide probe is coupled to a fluorophore being a donor for förster resonance energy transfer and the acceptor nucleotide probe is coupled to a fluorophore being an appropriate acceptor for förster resonance energy transfer.

A kit in molecular biology or in medical diagnostics is a package, which includes all necessary ingredients for performing a certain method or singular step. Standard chemicals as present in any standard molecular biology, chemical or medical laboratory are normally not included. Nevertheless, some of these standard chemicals may be indispensable to carry out the inventive assay or the method properly. It is understood that all ingredients are provided in quantities that allow for a proper execution of the desired reactions for the majority of scientific, diagnostic and industrial applications.

Often, but not always, these ingredients are provided in already prepared solutions ready- or close to ready-for-use. There may be also combinations of different ingredients already added together. A further advantage is that such kits use to be verified. Therefore, the operator doesn't have to prove again the viability of the diagnostic method and can save on at least some control experiments. Therefore kits are a very popular tool in laboratories in research, diagnostics and industry.

The following components may also be included in such kits: nucleoside triphosphates, transcription factor, co-factor of said nucleotide polymerase, reaction buffer, stopping buffer, microtiter plate suitable for the inventive assay (such as a white opaque plate), and blocking oligonucleotides.

DESCRIPTION OF THE FIGURES

FIG. 6: shows assay results of a substance test in the 1536-well microtiter plate format. The table shows a representation of the ratio of donor-(620 nm) and acceptor-fluorescence (665 nm). The rows of positive (C+) and negative control samples (C−) are indicated, further some primary hits are indicated in bold and in italics.

EXAMPLES

Figure 1:
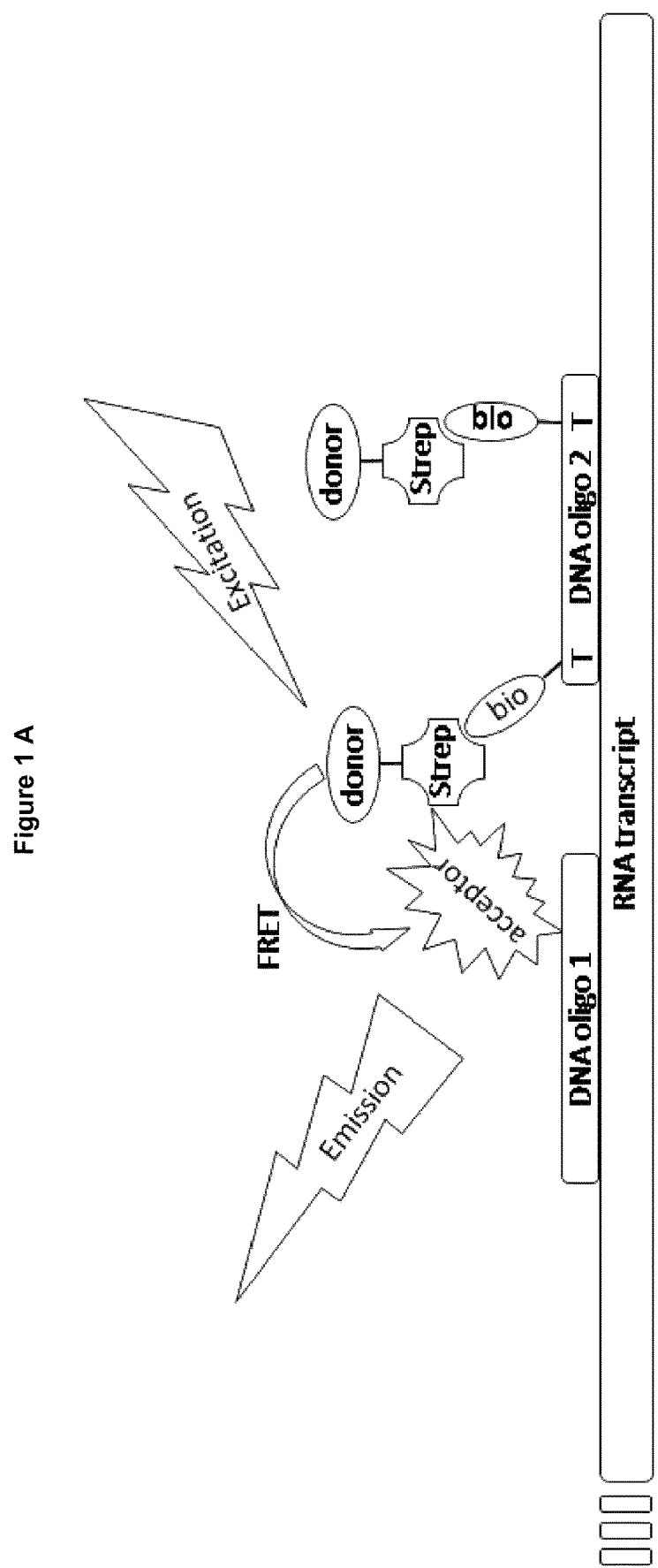
FIG. 1: shows the principle of detection of nucleotide polymerase activity based on FRET. Thereby bio represents biotin and Strep means streptavidin. $E_x$ and $E_M$ represent the energy used for extinction and the emitted energy (light at emission wavelength), respectively. A shows an embodiment wherein the fluorophores of the donor nucleotide probe are conjugated to the oligonucleotide using biotin/streptavidin. B shows an embodiment wherein the fluorophores of the donor and the acceptor nucleotide probe are covalently conjugated to the oligonucleotide. C shows an embodiment wherein the fluorophores of the acceptor nucleotide probe are conjugated to the oligonucleotide using biotin/streptavidin.
Figure 1B:
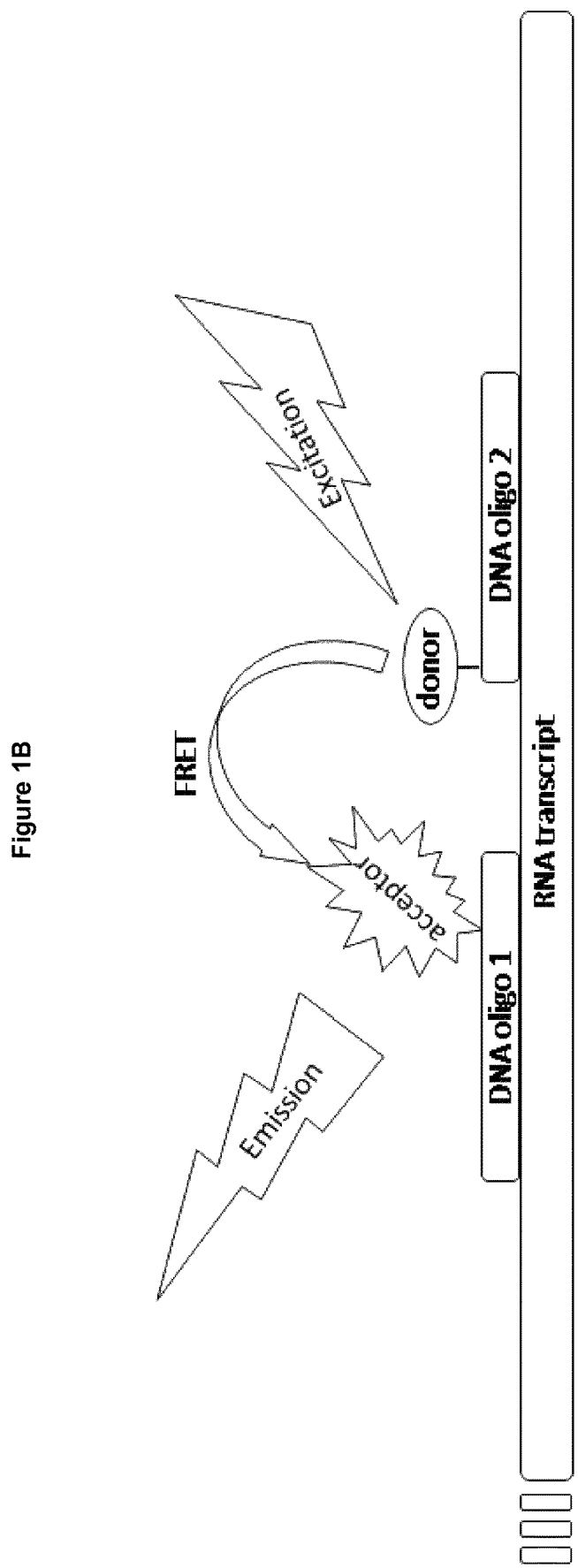
Figure 1C:
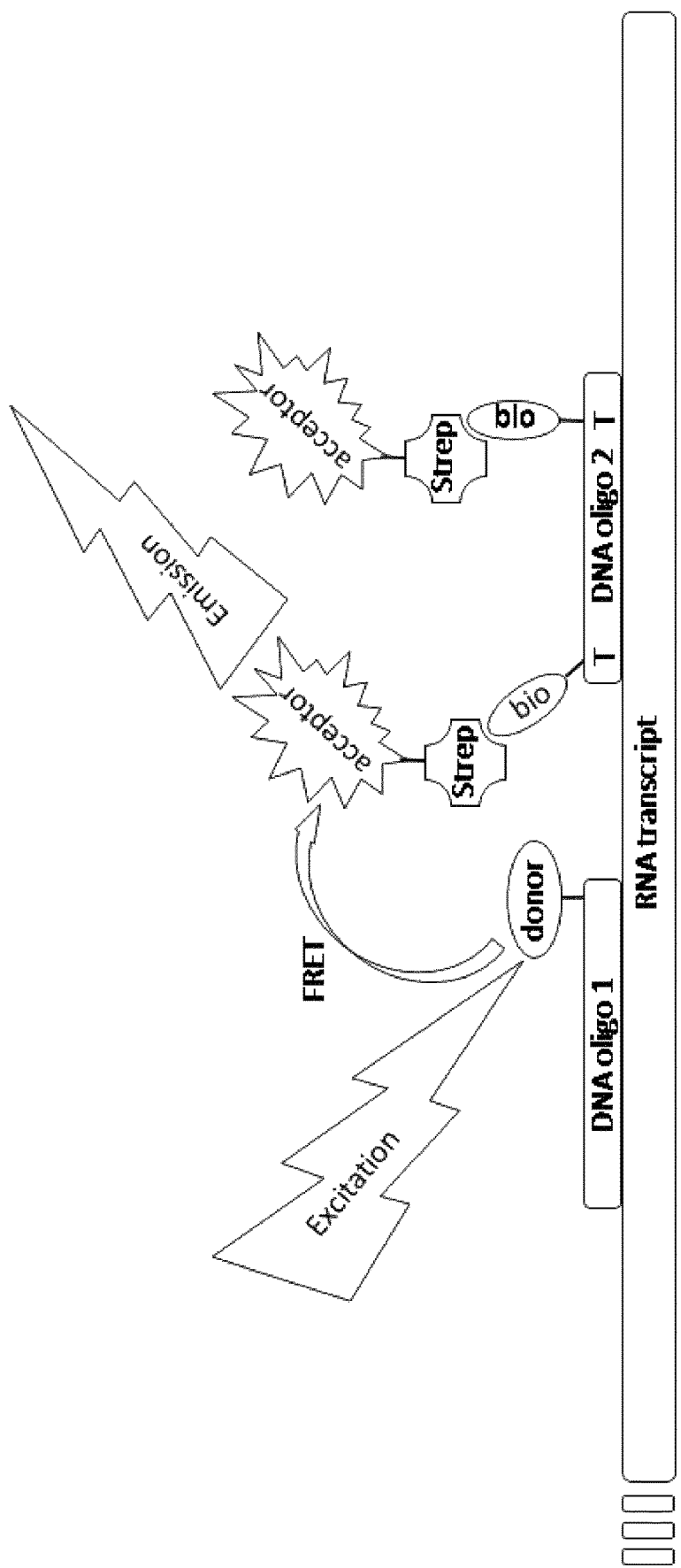
Figure 2:
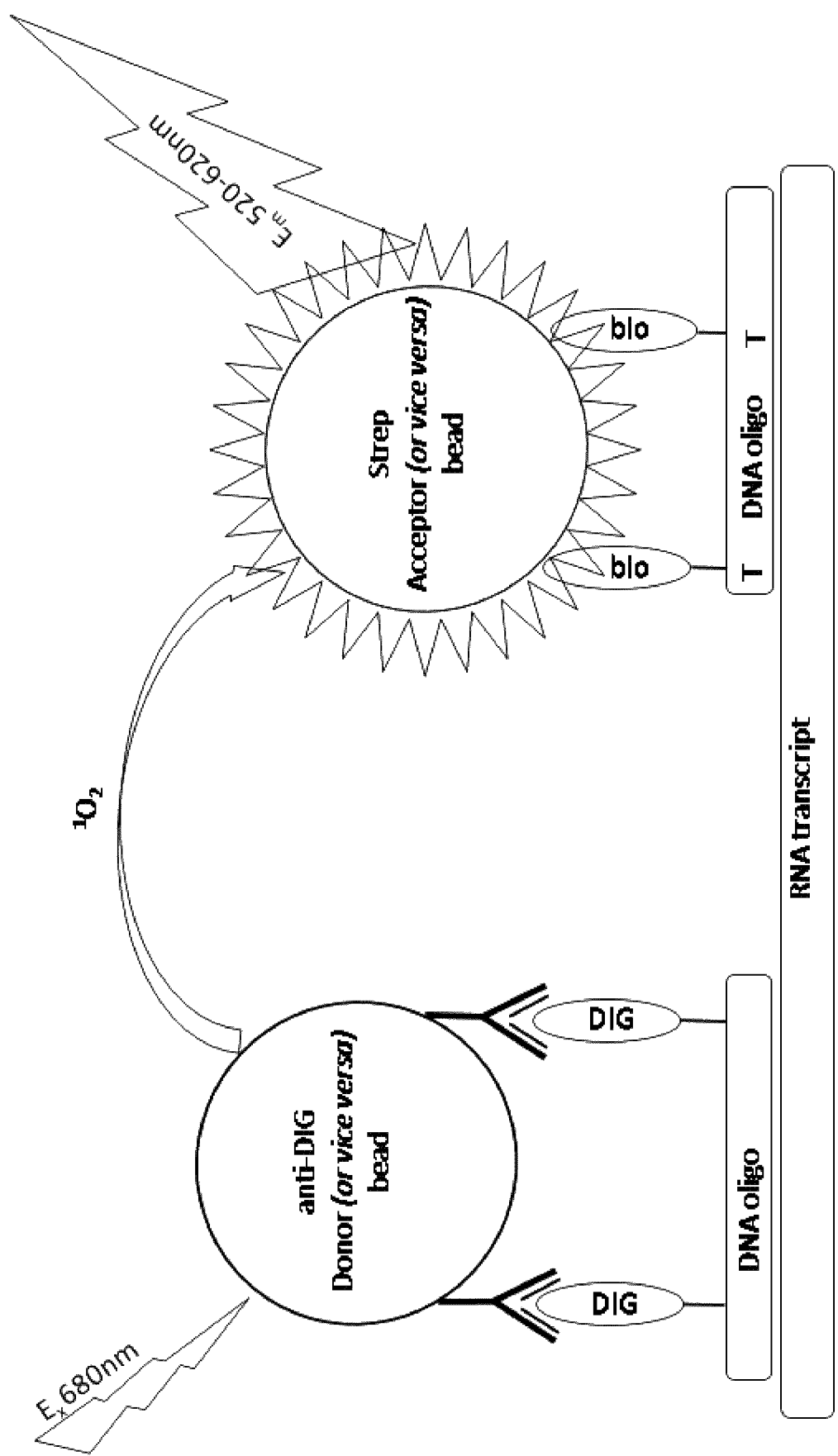
FIG. 2: shows the principle of detection of nucleotide polymerase activity based on Alpha technology. Thereby DIG means digoxygening, bio represents biotin and Strep means streptavidin. $E_x$ and $E_M$ represent the energy used for extinction and as the emitted energy (light at emission wavelength), respectively.

Example 1: Determination of Activity of Mitochondrial RNA-Polymerase in a High-Throughput Screening in the 1536-Well Plate Format The inventive method used monitors the activity of mitochondrial RNA-polymerase via detection of the formation of its product, a 407 bp long RNA sequence (SEQ ID No. 1). Detection of the product is facilitated by hybridization of two DNA-oligonucleotide probes to specific and adjacent sequences within the RNA product sequence. Upon annealing of the probes, two fluorophores that are coupled directly to an acceptor nucleotide probe (ATTO647, 5') or introduced via a coupled streptavidin interacting with a biothinylated donor nucleotide probe on the other side (Europium cryptate, 3') are brought into sufficient proximity to serve as a fluorescence-donor-acceptor pair. Thus, a FRET signal at 665 nm is generated upon excitation at 340 nm.

TABLE 1

Sequence of initiator and nucleotide probes used in example 1 and 2:

| Name | Sequence |
|---|---|
| Human LSP (top strand) | AAAGATAAAATTTGAAATCTGGTTAGGCTGGTGTTAGG GTTCTTTGTTTTTTGGGGTTTGGCAGAGATGTGTTTAAG TGCTGTGGCCAGAAGCGGGGAGGGGGGGTTTGGTGGA AATTTTTTGTTATGATGTCTGTGTGGAAAGTGGCTGTG CAGACATTCAATTGTTATTATTATGTCCTACAAGCATT AATTAATTAACACACTTTAGTAAGTATGTTCGCCTGTA ATATTGAACGTAGGTGCGATAAATAATAGGATGAGGCA GGAATCAAAGACAGATACTGCGACATAGGGTGCTCCGG CTCCAGCGTCTCGCAATGCTATCGCGTGCATACCCCCC AGACGAAAATACCAAATGCATGGAGAGCTCCCGTGAGT GGTTAATAGGGTGATAGACCTGTGATC |
| Probe No. 11 | ATTO47N-5'-ACAAAGAACCCTAACACCAG-3' |
| Probe No. 8 | bio-5'-AACACATCTCT(-bio)GCCAACCCCA-bio-3' |

The following Equipment and apparatus were used:
Thermo Multidrop®+Labcyte Echo®
Thermo Vario Teleshaker or Eppendorf Mixmate
Thermo Scientific Multifuge 1S-R+plate-rotor (384 well)
Perkin Elmer EnVision plate reader+TRF light unit
Assay Plate: Corning 3729 (1536, flat-bottom, non-binding, white) or Corning 3673 (384, low vol., round bottom, non-binding, white)

Proteins used as transcription factors (POLRMT: NP_005026.3, TFAM: NP_003192.1, TFB2M: NP_071761.1) are diluted from their stocks to working concentrations of 150 nM, 1.8 µM and 330 nM respectively, in a dilution buffer containing 100 mM TrisHCl pH 8.0, 200 mM NaCl, 10% (v/v) glycerol, 2 mM glutathione (GSH), 0.5 mM EDTA and 0.1 mg/mL bovine serum albumin (BSA). Protein dilutions and initiator (template DNA), comprising a pUC18 plasmid encoding the mitochondrial light strand promotor restriction linearized proximal to the promotor 3′-end (pUC-LSP), are mixed at the twofold final assay-concentration in a reaction buffer, containing 10 mM TrisHCl pH 7.5, 10 mM $MgCl_2$, 40 mM NaCl, 2 mM GSH, 0.01% (w/v) Tween-20 and 0.1 mg/mL BSA.

5 µL of this mix are dispensed, depending on the chosen microtiter plate format, using multi-channel pipettes or a Thermo Multidrop® dispenser into the wells of a microtiter plate and incubated at room-temperature (RT) for 10 minutes. Candidate substances in the assay are applied using contact-free acoustic droplet-dispensing (Labcyte Echo®) from 10 mM compound stocks in 100% DMSO, to a final concentration of 10 µM. Equal amounts of DMSO without any compound are added to positive control samples. An incubation step at RT for 10 minutes is applied to allow binding of compounds without having to compete with the natural nucleotide substrates.

The enzymatic reaction of the polymerase is started by the addition of 5 µL of a mix of dNTPs in reaction buffer to a final concentration of 500 µM each. No nucleotide triphosphate mix is added to negative control samples. The content of the wells is mixed using a Thermo Vario Teleshaker at 1500 rpm for 45 sec after which the microtiter plate is centrifuged at 500 g for 1 min. The enzymatic reaction samples are incubated for 2 hours at room-temperature. Plates may be incubated in a humidifying chamber at 100% humidity, to avoid evaporation.

In the meantime, a mix of the detection reagents is prepared in a buffer that is composed, such that the enzymatic reaction is terminated due to chelating of Mg-ions and increased ionic strength, containing 50 mM TrisHCl pH 7.5, 700 mM NaCl, 20 mM EDTA, and 0.01% (W/v) Tween-20. Eu-cryptate-coupled streptavidin is pre-incubated with a 100-fold molar excess of a random sequence oligonucleotide to block unspecific binding of single strand mRNA to the protein, for 10 min at RT in the dark. Afterwards, the blocked streptavidin(-Eu) is mixed with the nucleotide probes on ice and kept away from light until use.

At the end of the enzymatic reaction time 10 µL detection reagent mix is added, such that the final concentration of fluorescent-labeled donor nucleotide probe, fluorescent-labeled acceptor nucleotide probe in each assay well is 1 nM, and 3 nM respectively. Assay plates are again mixed and centrifuged as above and are stored at RT, protected from light for at least 2 h or until binding of the nucleotide probes to mRNA product of the polymerase leads to the development of the maximal FRET signal. A schematic overview of the assay workflow is depicted in FIG. 1.

The generated signal is measured with a suitable microtiter plate reader (Perkin Elmer EnVision plate reader, including TRF light unit), using excitation at 320 nm, an integration time of 200 µs and a delay time of 100 µs, before detection at 620 nm and 665 nm. The ratio of donor- and acceptor-fluorescence is used to assess the specific FRET as a measure of the generated polymerase product (i.e. enzymatic activity). Usually, the signal-to-background ratio (S:B) between positive and negative control samples is >10 and the signal homogeneity of positive and negative control was lower than 10% (CV %<10) resulting in z′ values >0.7.

According to this method small molecular weight substances have been tested for their effects on the mitochondrial transcription machinery in a high-throughput screen (HTS), at 10 µM final candidate substance concentration.

FIG. 6 is displaying a tabular representation of the results obtained during a screen of a library of small molecular weight compounds, for an exemplary 1536-well microtiter plate, comprising 1408 test wells and 64 wells each for positive and negative control samples. Based on the chosen hit-criteria (≤30% residual activity, relative to positive control). Primary hits on this plate were found in R15, X27, A44, B48 and T48. Activity data could be calculated based on fluorescence ratio values and normalized to positive (100%) and negative control samples (0%). One compound displaying inhibitory effects was identified with 13.7% activity on this plate. This finding is also representative for the generally observed hit-rate (0.05-0.1%) using larger substance libraries. As can be seen in FIG. 6, in addition to inhibition of the polymerase reaction, the assay format and specific conditions also allow for detection of apparently increased product formation, facilitating the identification of putative activators.

Figure 3:
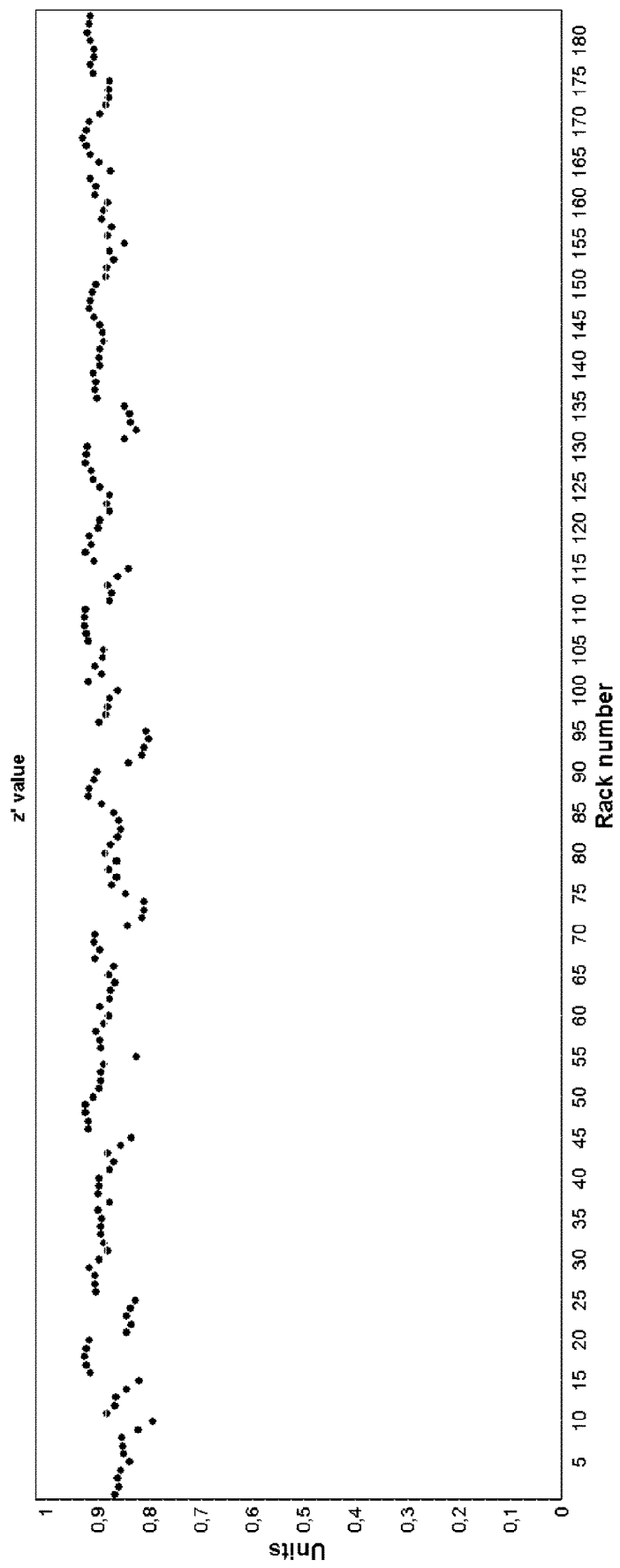
FIG. 3: shows a summary of the assay robustness during a HT-screening of a compound library. The z' values of individual plates, as a measure of assay robustness, were calculated and plotted for the 183 1536-well plates required to screen >250.000 compounds. The lower assay acceptance criterion is 0.4. The observed average z' value of 0.88 (white line) is indicated.
Figure 4:
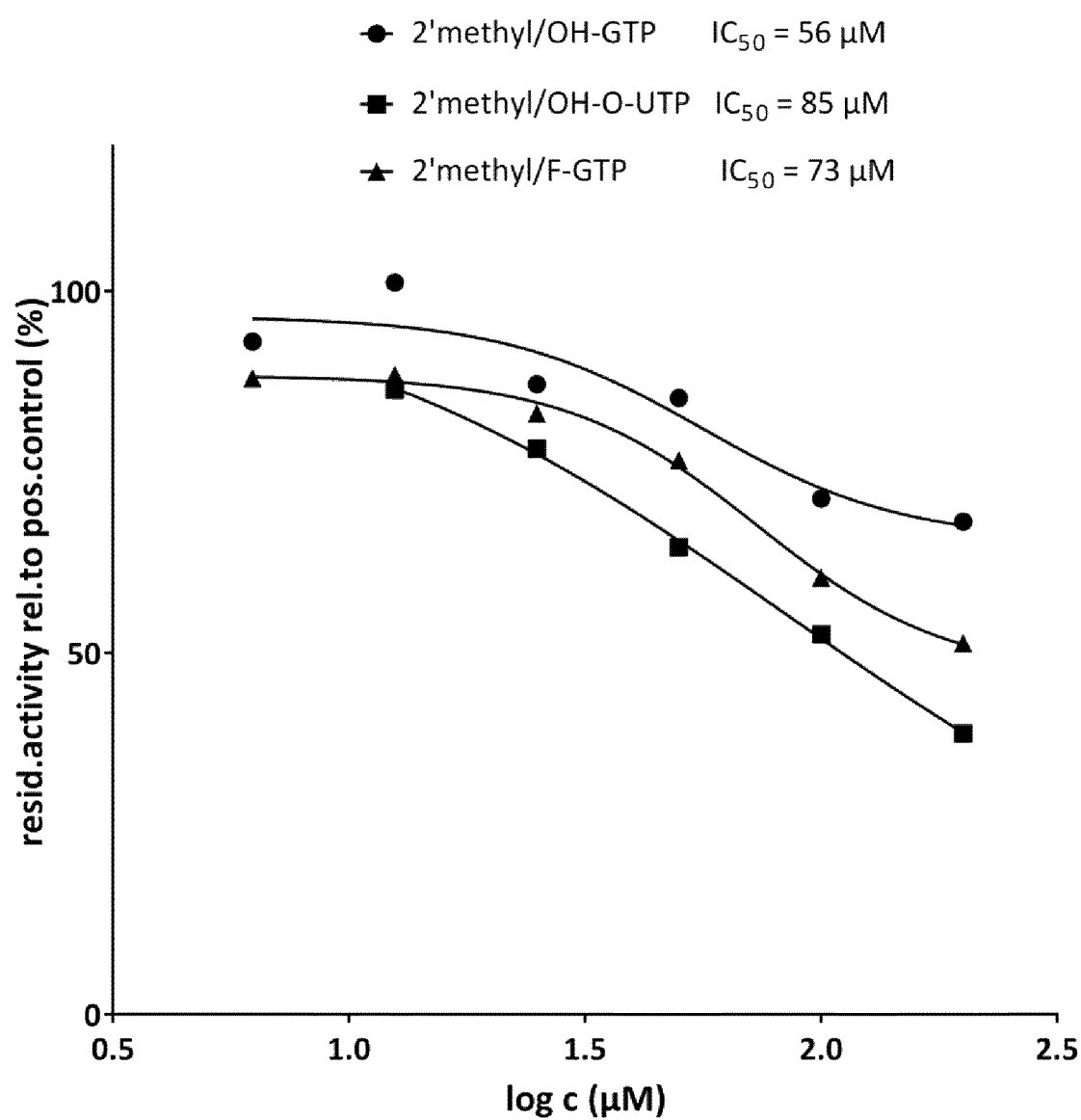
FIG. 4: shows a plot of resulting dose-dependent activity data obtained in example 2, an inventive method in 384-well microtiter plate format, yielding the concentration at which the enzymatic activity is reduced to 50% relative to the positive control sample ($IC_{50}$).
Figure 5:
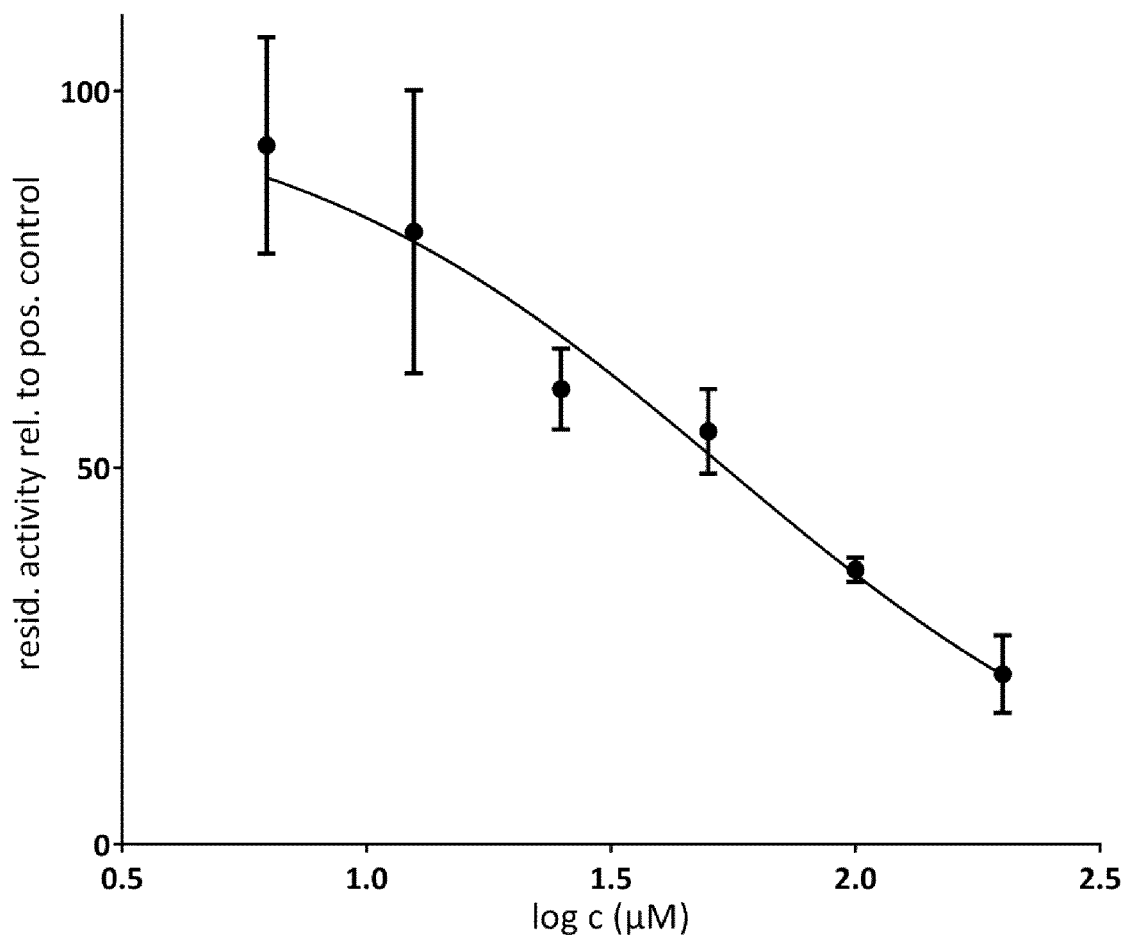
FIG. 5: shows resulting dose-dependent activity data of the nucleotide analogue TTTP in example 4 plotted and fitted to a four-parameter non-linear regression model, resulting in a sigmoidal curve, yielding the concentration at which the enzymatic activity is reduced to 50% relative to the positive control sample ($IC_{50}$).
Figure 7:
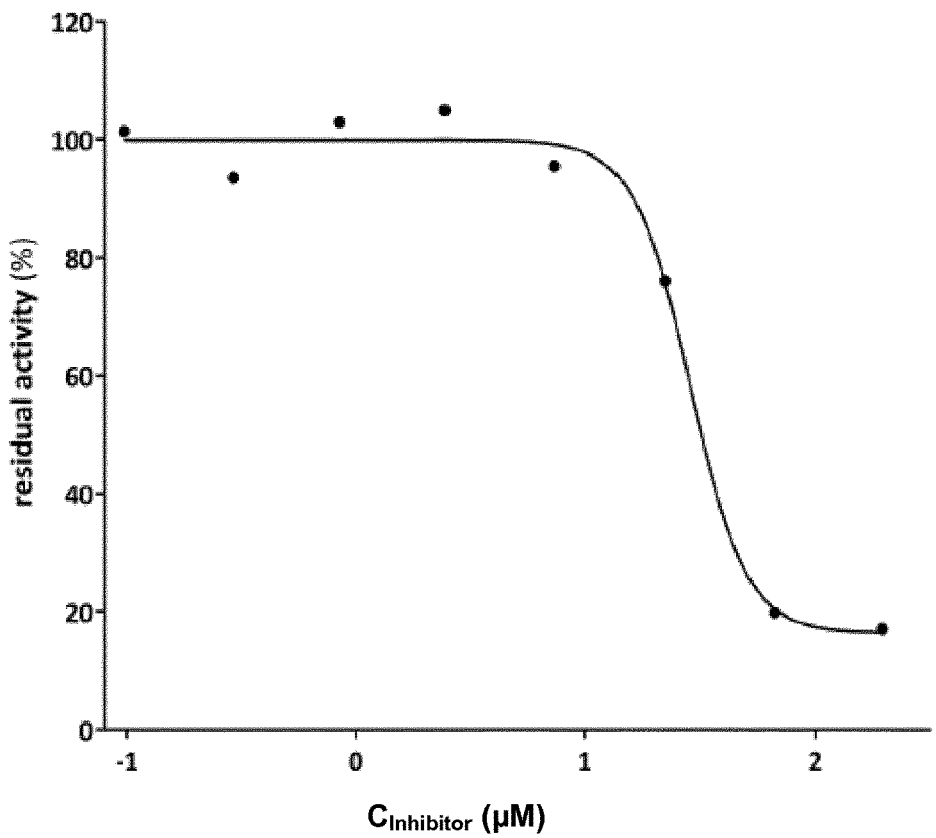
FIG. 7: is displaying the result obtained by example 5, describing $IC_{50}$-determination of a small molecular weight substance, starting from a maximal compound concentration of 200 µM to a lower limit of 90 nM. The substance had initially been identified as an inhibitor of the human POLRMT (mitochondrial DNA-directed RNA polymerase), with an $IC_{50}$<10 µM. It is apparent that the substance does also inhibit the bacteriophage T7 enzyme. These results exemplify that the general assay format is ideally suited to precisely differentiate effects of modulators on enzymes originating from different species.
Figure 8:
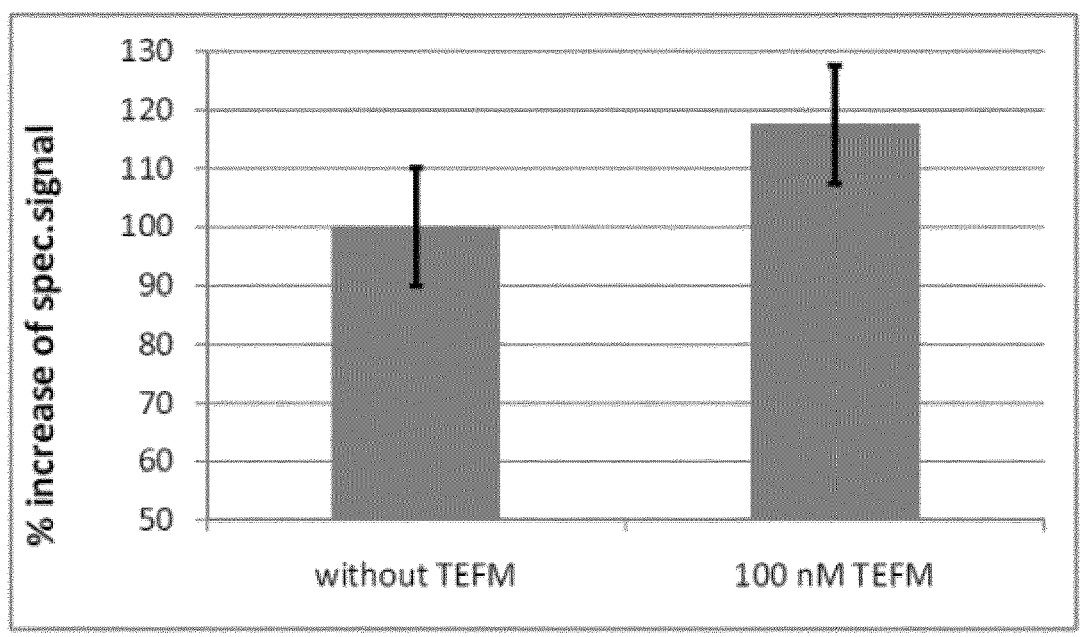
FIG. 8: is displaying the result of a comparative study of the effect of adding TEFM to the in vitro transcription reaction, as described in example 6. Two transcription reactions were set up either with or without the addition of TEFM (100 nM) and product formation quenched after 2 h. The specific FRET signal of the reaction without TEFM was used as a reference and normalized to 100%, while for the reaction including TEFM a signal increase of around 18% (±10%) was measured under the chosen conditions.

During a screen of 183 1536-well microtiter plates the calculated z′-values, as a measure of the assay robustness, were found to be consistently >0.75, with a mean value of 0.88 (see FIG. 3), giving reference of the observed homogeneity of positive and negative control samples.

A plot of the distribution of measured activity data of all sample wells during the exemplary high throughput screen yields the expected Gaussian curve around the positive control, with a slight shift towards lower activity. The latter can be explained, by the specific tuning of the assay conditions, which had been performed to suit the requirements of a search for inhibitors.

Example 2: Inhibitor Activity Determination in the 384-Well Plate Dose-Response Format The assay protocol largely corresponds to the setup described in example 1 (Determination of activity of mitochondrial RNA-polymerase using the same initiator and probes than in example 1). For determination of the activity, however, the reaction mix always contains the nucleotide triphosphate mix, to enforce potential competition between inhibitor compound and substrate. Negative control samples are set up such that no template DNA (pUC-LSP) is included in the reaction mixture.

Pre-diluted protein samples are mixed with the dNTP-mixture in a reaction buffer, containing 10 mM TrisHCl pH 7.5, 10 mM $MgCl_2$, 40 mM NaCl, 2 mM GSH, 0.01% (w/v) Tween-20 and 0.1 mg/mL BSA, to yield final assay concentrations of 7.5 nM (POLRMT), 90 nM (TFAM), 20 nM (TFB2M) and 500 µM (dNTPs). 5 µL of this mix are dispensed, depending on the chosen microtiter plate format, using multi-channel pipettes or a Thermo Multidrop® dispenser into the wells of a microtiter plate and incubated at room-temperature (RT) for 10 minutes.

Candidate substances in the assay are applied using contact-free acoustic droplet-dispensing (Labcyte Echo®) from 10 mM compound stocks (in 100% DMSO) in an appropriate 8-point dilution series to ensure accurate fitting of the resulting activity data (i.e. upper and lower asymptote reached). Equal amounts of DMSO without any compound are added to positive control samples. An incubation step at RT for 10 minutes is applied to allow binding of compounds.

The enzymatic reaction is started by the addition of 5 µL of a mix of template DNA (pUC-LSP) in reaction buffer to a final concentration of 0.5 nM. The following mixing, incubation and detection steps correspond to the steps described in example 1. The resulting dose-dependent activity data is plotted and fitted to a four-parameter non-linear regression model, resulting in a sigmoidal curve, yielding the concentration at which the enzymatic activity is reduced to 50% relative to the positive control sample ($IC_{50}$).

Table 2 is displaying an overview of the results obtained during $IC_{50}$-determination of a series of inhibitors of different activity, starting from a maximal compound concentration of 200 μM to a lower limit of 5 μM. Based on the chosen concentrations of the test enzymes and scrutinized compounds the $IC_{50}$-values observed for this assay format typically span four to five orders of magnitude, indicating the wide dynamic range of the assay system. Other tests have successfully been performed using reduced enzyme concentrations, allowing for a lower limit of detection of inhibition at 3 nM.

Pre-diluted protein samples are mixed with the dNTP-mixture in a reaction buffer, containing 10 mM TrisHCl pH 7.5, 10 mM $MgCl_2$, 40 mM NaCl, 2 mM GSH, 0.01% (w/v) Tween-20 and 0.1 mg/mL BSA, to yield final assay concentrations of 40 nM (mPOLRMT), 80 nM (mTFAM), 80 nM (mTFB2M) and 500 μM (dNTPs). This setup accommodates for the lower enzymatic activity of the employed preparation of the mouse enzyme compared to the human homolog.

TABLE 2

Assay results obtained for an $IC_{50}$ determination of different compounds in the 384-well microtiter plate format. The calculated z'-value during this experiment was 0.88, signal-to-background (S:B) = 10.2, signal-to-noise (S:N) = 49.7.

| Sample ID | Highest assayconc. [μM] | Hill slope | $IC_{50}$ (μM) | res. activity at highest conc. (%) | res. activity at lowest conc. (%) | $R^2$ |
|---|---|---|---|---|---|---|
| 2'methyl/OH-GTP | 200 | −2.05 | 56.2 | 65.5 | 96.5 | 0.9076 |
| 2'methyl/OH-O-UTP | 200 | −0.85 | 84.5 | 8.6 | 102 | 0.9988 |
| 2'methyl/F-GTP | 200 | −2.15 | 73.4 | 46.9 | 88.32 | 0.9962 |

Example 3: Inhibitor Activity Determination, Using Mouse Mitochondrial RNA-Polymerase, in a 384-Well Plate Dose-Response Format The assay protocol largely corresponds to the setup described in example 2 for determination of the $IC_{50}/EC_{50}$ for modulators of the activity of the human enzyme. However, proteins utilized in this embodiment are NM_172551.3 (mPOLRMT), NM_008249.4 (mTFB2M) and NM_009360.4 (mTFAM). Furthermore the initiator, or DNA transcription template corresponds to the murine mitochondrial light-strand promotor (mLSP), encoded in a pCRY-TOPO plasmid and restriction linearized proximal to the 3'-end of the promotor, to allow for a 'run-off' transcription reaction. As a consequence, the sequences of the employed DNA-probes had to be adjusted for complementarity to the promotor-transcript sequence.

TABLE 3

Sequence of initiator and nucleotide probes used in example 3:

| Name | Sequence |
|---|---|
| Murine LSP (top strand) | TTTGGTTCACGGAACATGATTTTGTAAAATTTTTACAA GTACTAAAATATAAGTCATATTTTGGGAACTACTAGAA TTGATCAGGACATAGGGTTTGATAGTTAATATTATATG TCTTTCAAGTTCTTAGTGTTTTTGGGGTTTGGCATTAA GAGGAGGGGGTGGGGGGTTTGGAGAGTTAAAATTTGGT ATTGAGTAGCATTTATGTCTAACAAGCATGAATAATTA GCCTTAGGTGATTGGGTTTTGCGGACTAATGATTCTTC ACCGTAGGTGCGTCTAGACTGTGTGCTGTCCTTTCATG CCTTGACGGCTATGTT |
| Probe No. 6 | bio-5'-TAACT(bio)ATCAAACCCTATGT-3'-bio |
| Probe No. 7 | 5'-AACTTGAAAGACATATAAT-3'-ATTO647N |

For determination of the activity, however, the reaction mix always contains the nucleotide triphosphate mix, to enforce potential competition between inhibitor compound and substrate. Negative control samples are set up such that no template DNA (pUC-LSP) is included in the reaction mixture.

However, this observation might be related to the production of the enzyme samples and determination of the optimal polymerase concentration is necessary for any enzyme tested. Also, for this particular embodiment it was found that a ratio of polymerase and transcription factors of 1:2:2 yields the highest productivity and, thus best assay performance.

5 μL of this reaction mixture are dispensed, depending on the chosen microtiter plate format, using multi-channel pipettes or a Thermo Multidrop® dispenser into the wells of a microtiter plate and incubated at room-temperature (RT) for 10 minutes.

Candidate substances tested in this example are applied using contact-free acoustic droplet-dispensing (Labcyte Echo®) from 10 mM compound stocks (in 100% DMSO) in an appropriate 8-point dilution series to ensure accurate fitting of the resulting activity data (i.e. upper and lower asymptote reached). Equal amounts of DMSO without any compound are added to positive control samples. An incubation step at RT for 10 minutes is applied to allow binding of compounds.

The enzymatic reaction is started by the addition of 5 μL of a mix of template DNA (mLSP) in reaction buffer to a final concentration of 5 nM. The following mixing, incubation and detection steps correspond to example 2.

The resulting dose-dependent activity data is plotted and fitted to a four-parameter non-linear regression model, resulting in a sigmoidal curve, yielding the concentration at which the enzymatic activity is reduced to 50% relative to the positive control sample ($IC_{50}$).

Table 4 is displaying the result obtained during $IC_{50}$-determination of a small molecular weight substance, starting from a maximal compound concentration of 1 μM to a lower limit of 0.25 nM. The substance had initially been identified as an inhibitor of the human POLRMT enzyme with an $IC_{50\text{-}human}$ ~1 nM. Despite the higher enzyme concentration applied in this assay format, it is apparent that the substance does also inhibit the mouse enzyme, however with ~20-fold higher $IC_{50}$. These results exemplify that the general assay format is ideally suited to precisely differentiate effects of modulators of the enzymatic activity, even at very low substance concentrations.

TABLE 4

Assay result obtained for an $IC_{50}$ determination in the 384-well microtiter plate format The calculated z'-value during this experiment was ~0.6, signal-to-background (S:B) = 3.1, signal-to-noise (S:N) = 13.7.

| Sample ID | Highest assay conc. [μM] | Hill slope | $IC_{50}$ (μM) | res. activity at highest conc. (%) | res. activity at lowest conc. (%) |
|---|---|---|---|---|---|
| Compound 197459 | 1 | −0.058 | 0.02 | 31.85 | 95.54 |

Example 4: Inhibitor Activity Determination, Using Human Mitochondrial DNA-Polymerase, in a 384-Well Plate Dose-Response Format The assay protocol largely corresponds to the setup described in example 1 (Determination of activity of mitochondrial RNA-polymerase using the same initiator and probes than in example 1). For determination of the activity of the mitochondrial replication, however, the two-subunit complex of the mitochondrial DNA-polymerase (POLG, NM_002693.2, NM_007215.3), the transcription factor TWINKLE (NM_021830.4) and mitochondrial single-strand binding protein (SSBP1, NM_001256510.1) are used. Also, the reaction mix always contains the substrate nucleotide mix, to enforce potential competition between inhibitor compound and substrate.

For DNA-replication the template is generated using a circular, single-stranded DNA formed from pBlueskript SK+. To this circular, ssDNA, a primer with 42-nucleotide poly-T is annealed to form a fork structure. To make dsDNA, the primer is elongated with KOD polymerase, which synthesizes DNA around the entire circle, until again it reaches the primer. At this point DNA-synthesis stops and a double-stranded DNA template of about 3000 bp with an artificial replication fork is formed. After this, the template is purified and used in the assay for a rolling circle DNA replication, which yields a product of repetitive stretches of the sequence displayed in Table 2.

For activity determination, negative control samples are set up such that no template DNA is included in the assay mixture. Assay components are mixed in a buffer containing 25 mM TrisHCl pH 8.0, 5 mM $MgCl_2$, 2 mM GSH, and 0.1 mg/mL BSA, to yield final assay concentrations of 30 nM POLG, 15 nM TWINKLE, 20 nM SSBP1, 250 μM dNTPs, 4 mM ATP as well as the two DNA-probes at 3 nM concentration each.

5 μL of this mix are dispensed, depending on the chosen microtiter plate format, using multi-channel pipettes or a Thermo Multidrop® dispenser into the wells of a microtiter plate and incubated at room-temperature (RT) for 10 minutes.

Chemical compounds under scrutiny in the assay are applied using contact-free acoustic droplet-dispensing (Labcyte Echo®) from 10 mM compound stocks (in 100% DMSO) in an appropriate 8-point dilution series to ensure accurate fitting of the resulting activity data (i.e. upper and lower asymptote reached). Equal amounts of DMSO without any compound are added to positive control samples. An incubation step at RT for 10 minutes is applied to allow binding of compounds.

The enzymatic reaction is started by the addition of 5 μL of a mix template DNA in reaction buffer to a final concentration of 5 nM. Following incubation for 1 h at 37° C., the reaction is stopped by addition of a detection mix, containing 3 nM streptavidin-coupled Eu-cryptate pre-incubated with an excess of an unspecific random oligonucleotide, in 20 mM Tris-HCl pH 8.0, 400 mM NaCl and 50 mM EDTA. HTRF-signals are measured following over-night incubation at room-temperature.

The resulting dose-dependent activity data is plotted and fitted to a four-parameter non-linear regression model, resulting in a sigmoidal curve, yielding the concentration at which the enzymatic activity is reduced to 50% relative to the positive control sample ($IC_{50}$).

Table 5 is displaying the results obtained during $IC_{50}$-determination of a nucleotide-analogue inhibitor of POLG, starting from a maximal compound concentration of 200 μM to a lower limit of 5 μM. Based on the chosen concentrations of the nucleotide substrate ($C_{(dNTP)}$=250 μM) and the scrutinized compound, the resulting $IC_{50}$-value is well within the expected range, indicating direct competition between the substrate nucleotides and the nucleotide-analogue inhibitor.

TABLE 5

Assay results obtained for an $IC_{50}$ determination of the nucleotide analogue TTTP The calculated z'-value during this experiment was 0.7, signal-to-background (S:B) = 9.2.

| Sample ID | Highest assay conc. [μM] | Hill slope | $IC_{50}$ (μM) | res. activity at highest conc. (%) | res. activity at lowest conc. (%) | $R^2$ |
|---|---|---|---|---|---|---|
| 4-Thiothymidine-5'-Triphosphate | 200 | −0.9462 | 54.07 | 22.6 | 92.79 | 0.8693 |

TABLE 6

Sequence of initiator and nucleotide probes used in example 4:

| Name | Sequence |
|---|---|
| 'rolingcircle' replicationproduct | 5'-ATAGGGGTATGAAATTTGAAATCTGGTT AGGCTGGTGTTAGGGTTCTTTGTTTTTGGGG TTTGGCAGAGATGTGTTTAAGTGCTGTGGCC ACATACCCCTC-3' |
| Probe No. 11 | ATTO647N-5'-ACAAAGAACCCTAACACCAG-3' |
| Probe No. 13 | bio-5'-AACACATCTCT(-bio)GCCAAA CCCCA-bio-3' TGGGGTTTGGCAGAGAT |

Example 5: Assay Protocol for Inhibitor Activity Determination, Using Bacteriophage T7 RNA-Polymerase, in the 384-Well Plate Dose-Response Format Assay principle, background and equipment correspond to the setup described in example 1. The assay protocol largely corresponds to the setup of example 2 describing the general application in determination of the $IC_{50}/EC_{50}$ for modulators of the activity of the human enzyme. However, the polymerase utilized in this assay version is the bacteriophage T7 RNA-polymerase, which can be acquired from diverse commercial sources.

The present assay does not require the presence of any ancillary factors. Instead, a linear DNA transcription template which is shown by SEQ ID No. 21 and SEQ ID No. 22 as well as in table 7 is generated (e.g. via primer hybridization), which enables transcription initiation by the polymerase alone. Thus, monitoring the effect of small molecular modulators on the activity of the RNA-polymerase is achieved, free from artifacts that might be caused by compound binding to transcription factors. In the specific case of the bacteriophage T7 enzyme, a single-stranded overhang is not even required as transcription activity of this polymerase relies on a double-stranded DNA template.

TABLE 7

Sequence of linear DNA transcription template used in example 5:

| Name | Sequence |
| --- | --- |
| linear transcription template | 5'-GGCGGGAGAAGAATTTGAAATCTGGTTAGGCTGGTG<br>3'-CGGCGGCCCTTTTTTCCGCCCTCTTCTTAAACTTTAGACCAATCCGACCAC<br><br>TTAGGGTTCTTTGTTTTTGGGGTTTGGCAGAGATGTGTTTAAGTGCTGTGGC<br>AATCCCAAGAAACAAAAACCCCAAACCGTCTCTACACAAATTCACGACACCG<br>CAGAAGCGGGG-3' (SEQ ID No. 21)<br>GTCTTCGCCCC-5' (SEQ ID No. 22) |

For determination of the activity, the reaction mix always contains the substrate nucleotide mix, to enforce potential competition between the tested inhibitor compound and the substrate. Negative control samples are set up such that no template DNA is included in the assay mixture. Pre-diluted enzyme samples are mixed with the dNTP-mixture in a reaction buffer, containing 10 mM TrisHCl pH 7.5, 10 mM $MgCl_2$, 40 mM NaCl, 2 mM GSH, 0.01% (w/v) Tween-20 and 0.1 mg/mL BSA, to yield final assay concentrations of 50 nM (T7 RNA-polymerase) and 500 µM (dNTPs). 5 µL of this mix are dispensed, depending on the chosen microtiter plate format, using multi-channel pipettes or a Thermo Multidrop® dispenser into the wells of a (low protein-binding) microtiter plate and incubated at room-temperature (RT) for 10 minutes.

The chemical compound under scrutiny in the assay was 4-methyl-5-[2-(pyrimidin-2-ylamino)thiazol-4yl]thiazol-2-amine (available at ChemDiv) and is applied using contact-free acoustic droplet-dispensing (Labcyte Echo®) from 10 mM compound stocks (in 100% DMSO) in an appropriate 8-point dilution series to ensure accurate fitting of the resulting activity data (i.e. upper and lower asymptote reached). Equal amounts of DMSO without any compound are added to positive control samples. An incubation step at RT for 10 minutes is applied to allow binding of compounds. The enzymatic reaction is started by the addition of 5 µL of a mix of template DNA in reaction buffer to a final concentration of 2 nM. The following mixing, incubation and detection steps correspond to example 2.

The resulting dose-dependent activity data is plotted and fitted to a four-parameter non-linear regression model, resulting in a sigmoidal curve, yielding the concentration at which the enzymatic activity is reduced to 50% relative to the positive control sample ($IC_{50}$).

Example 6: Determination of Activity of Mitochondrial RNA-Polymerase with and without TEFM To enhance the enzymatic turnover and, thus, specific signal intensity of the mitochondrial in vitro transcription reaction, the mitochondrial transcription elongation factor (TEFM, NP_078959.3.) can be added to the assay reagent mixture.

The general workflow of the assay and composition of assay reagents are described in Posse et al (Nucl. Acids Res. 2015). A linearized pUC18 plasmid comprising the human mitochondrial light-strand promotor sequence (LSP) is used as transcription plasmid.

Adaptations made to the original protocol relate to the different detection method applied and correspond to the set-up described in example 1. Hence, instead of the addition and later scintillation detection of radio-isotope labeled nucleotide, only non-radioactive nucleotides are used and the detection of product formation is again based on the addition and specific binding of DNA oligonucleotide probes, labeled with fluorescent dyes to constitute a FRET pair.

The invention claimed is:

1. A method for detection of nucleotide polymerase activity comprising the following steps:
  a) providing a reaction mixture comprising at least said polymerase, an initiator, and nucleoside triphosphates,
  b) providing conditions sufficient to allow the polymerase an assembling of nucleotides,
  c) stopping polymerase assembling of nucleotides,
  d) after the step of stopping polymerase assembling of nucleotides, adding a donor nucleotide probe and an acceptor nucleotide probe wherein said donor nucleotide probe is conjugated to a first non-radioactive label and said acceptor nucleotide probe is conjugated to a second non-radioactive label, wherein said labels allow determination of close proximity of said nucleotide probes,
  e) providing conditions sufficient to allow the nucleotide probes to hybridize with the product of step b) and
  f) determining if said donor and acceptor nucleotide probes are in close proximity wherein close proximity correlates with the activity of the nucleotide polymerase wherein said initiator is a template oligonucleotide or a primer for a template-independent nucleotide polymerase, and wherein said donor nucleotide probe and said acceptor nucleotide probe are complementary to the product of the nucleotide polymerase assembled at step b).

2. The method according to claim 1, wherein the label of the donor nucleotide probe and the label of the acceptor nucleotide probe allow energy transfer which can be determined in step f).

3. The method according to claim 1, wherein the reaction mixture further comprises a candidate substance to test its effect on the nucleotide polymerase activity.

4. The method according to claim 3, wherein providing a reaction mixture of step a) comprises the following:
   1) contacting said polymerase with the initiator, at least one transcription factor and an appropriate co-factor of the nucleotide polymerase resulting in a first reaction mixture
   2) incubating said first reaction mixture
   3) adding to said first reaction mixture the candidate substance resulting in a second reaction mixture
   4) incubating said second reaction mixture
   5) adding to said second reaction mixture nucleoside triphosphates.

5. The method according to claim 1, wherein the reaction mixture of step a) comprises further at least one transcription factor, replication factor or co-factor of the nucleotide polymerase.

6. The method according to claim 1, wherein the nucleotide polymerase is selected from the group consisting of DNA dependent DNA polymerase, RNA dependent DNA polymerase, DNA dependent RNA polymerase, RNA dependent RNA polymerase, independent RNA polymerase, and independent DNA polymerase.

7. The method according to claim 1, wherein the donor nucleotide probe or the acceptor nucleotide probe is conjugated to a label or fluorophore by covalent bonding or by non-covalent interaction.

8. The method according to claim 1, wherein the donor nucleotide probe or the acceptor nucleotide probe is conjugated to a label or fluorophore by non-covalent interaction mediated by biotin covalently coupled to the donor nucleotide probe or respectively the acceptor nucleotide probe and streptavidin covalently coupled to the label or fluorophore.

9. The method according to claim 8, wherein unspecific binding of the streptavidin covalently coupled to the label or fluorophore is blocked using random oligonucleotides before the streptavidin covalently coupled to the label or fluorophore is conjugated to the biotin covalently coupled to the donor nucleotide probe or the acceptor nucleotide probe.

10. The method according to claim 1, wherein the donor nucleotide probe and the acceptor nucleotide probe are used in a ratio between 1:2 and 2:1.

11. The method according to claim 1, wherein the method is adapted to be carried out as a homogenous high throughput screen.

12. The method according to claim 1, wherein the method is carried out at room temperature.

13. A method for detection of nucleotide polymerase activity comprising the following steps:
   a) providing a reaction mixture comprising said polymerase, an initiator, and nucleoside triphosphates,
   b) providing conditions sufficient to allow the polymerase an assembling of nucleotides,
   c) stopping polymerase assembling of nucleotides,
   d) after the step of stopping polymerase assembling of nucleotides, adding a donor nucleotide probe and an acceptor nucleotide probe wherein the donor nucleotide probe is conjugated to a fluorophore being a donor for förster resonance energy transfer and the acceptor nucleotide probe is conjugated to a fluorophore being a fluorescence quencher or an appropriate acceptor for förster resonance energy transfer,
   e) providing conditions sufficient to allow the nucleotide probes to hybridize with the product of step b) and
   f) determining fluorescence wherein said fluorescence correlates with the activity of the nucleotide polymerase;
   wherein said initiator is a template oligonucleotide or a primer for a template-independent nucleotide polymerase, and
   wherein said donor nucleotide probe and said acceptor nucleotide probe are complementary to the product of the nucleotide polymerase assembled at step b).

14. The method according to claim 13, wherein the reaction mixture further comprises a candidate substance to test its effect on the nucleotide polymerase activity.

15. The method according to claim 14, wherein providing a reaction mixture of step a) comprises the following:
   1) contacting said polymerase with the initiator, at least one transcription factor and an appropriate co-factor of the nucleotide polymerase resulting in a first reaction mixture
   2) incubating said first reaction mixture
   3) adding to said first reaction mixture the candidate substance resulting in a second reaction mixture
   4) incubating said second reaction mixture
   5) adding to said second reaction mixture nucleoside triphosphates.

16. The method according to claim 13, wherein the reaction mixture of step a) comprises further at least one transcription factor, replication factor or co-factor of the nucleotide polymerase.

17. The method according to claim 13, wherein the nucleotide polymerase is selected from the group consisting of DNA dependent DNA polymerase, RNA dependent DNA polymerase, DNA dependent RNA polymerase, RNA dependent RNA polymerase, independent RNA polymerase, and independent DNA polymerase.

18. The method according to claim 13, wherein the donor nucleotide probe or the acceptor nucleotide probe is conjugated to a label or fluorophore by covalent bonding or by non-covalent interaction.

19. The method according to claim 13, wherein the donor nucleotide probe or the acceptor nucleotide probe is conjugated to a label or fluorophore by non-covalent interaction mediated by biotin covalently coupled to the donor nucleotide probe or respectively the acceptor nucleotide probe and streptavidin covalently coupled to the label or fluorophore.

20. The method according to claim 19, wherein unspecific binding of the streptavidin covalently coupled to the label or fluorophore is blocked using random oligonucleotides before the streptavidin covalently coupled to the label or fluorophore is conjugated to the biotin covalently coupled to the donor nucleotide probe or the acceptor nucleotide probe.

21. The method according to claim 13, wherein the donor nucleotide probe and the acceptor nucleotide probe are used in a ratio between 1:2 and 2:1.

22. The method according to claim 13, wherein the method is adapted to be carried out as a homogenous high throughput screen.

23. The method according to claim 13, wherein the method is carried out at room temperature.

* * * * *

SEQUENCE LISTING

<160> NUMBER OF SEQ ID NOS: 22

<210> SEQ ID NO 1
<211> LENGTH: 407
<212> TYPE: DNA
<213> ORGANISM: Homo sapiens

<400> SEQUENCE: 1

| | | | | | |
|---|---|---|---|---|---|
| aaagataaaa | tttgaaatct | ggttaggctg | gtgttagggt | tctttgtttt | tggggtttgg | 60 |
| cagagatgtg | tttaagtgct | gtggccagaa | gcggggagg | gggggtttgg | tggaaatttt | 120 |
| ttgttatgat | gtctgtgtgg | aaagtggctg | tgcagacatt | caattgttat | tattatgtcc | 180 |
| tacaagcatt | aattaattaa | cacactttag | taagtatgtt | cgcctgtaat | attgaacgta | 240 |
| ggtgcgataa | ataataggat | gaggcaggaa | tcaaagacag | atactgcgac | ataggtgct | 300 |
| ccggctccag | cgtctcgcaa | tgctatcgcg | tgcatacccc | ccagacgaaa | ataccaaatg | 360 |
| catggagagc | tcccgtgagt | ggttaatagg | gtgatagacc | tgtgatc | | 407 |

<210> SEQ ID NO 2
<211> LENGTH: 320
<212> TYPE: DNA
<213> ORGANISM: Mus musculus

<400> SEQUENCE: 2

| | | | | | |
|---|---|---|---|---|---|
| tttggttcac | ggaacatgat | tttgtaaaat | ttttacaagt | actaaaatat | aagtcatatt | 60 |
| ttgggaacta | ctagaattga | tcaggacata | gggtttgata | gttaatatta | tatgtctttc | 120 |
| aagttcttag | tgtttttggg | gtttggcatt | aagaggaggg | ggtgggggt | ttggagagtt | 180 |
| aaaatttggt | attgagtagc | atttatgtct | aacaagcatg | aataattagc | cttaggtgat | 240 |
| tgggttttgc | ggactaatga | ttcttcaccg | taggtgcgtc | tagactgtgt | gctgtccttt | 300 |
| catgccttga | cggctatgtt | | | | | 320 |

<210> SEQ ID NO 3
<211> LENGTH: 114
<212> TYPE: DNA
<213> ORGANISM: Artificial Sequence
<220> FEATURE:
<223> OTHER INFORMATION: sequence of tailed template

<400> SEQUENCE: 3

| | | | | | |
|---|---|---|---|---|---|
| ccccgcttct | ggccacagca | cttaaacaca | tctctgccaa | accccaaaaa | caaagaaccc | 60 |
| taacaccagc | ctaaccagat | ttcaaattct | tctcccgcct | tttttcccgg | cggc | 114 |

<210> SEQ ID NO 4
<211> LENGTH: 99
<212> TYPE: DNA
<213> ORGANISM: Artificial Sequence
<220> FEATURE:
<223> OTHER INFORMATION: sequence of tailed template

<400> SEQUENCE: 4

| | | | | | |
|---|---|---|---|---|---|
| ggcgggagaa | gaatttgaaa | tctggttagg | ctggtgttag | ggttctttgt | ttttggggtt | 60 |
| tggcagagat | gtgtttaagt | gctgtggcca | gaagcgggg | | | 99 |

<210> SEQ ID NO 5
<211> LENGTH: 101
<212> TYPE: DNA
<213> ORGANISM: Artificial Sequence
<220> FEATURE:
<223> OTHER INFORMATION: roling-circle template

```
<400> SEQUENCE: 5
ataggggtat gaaatttgaa atctggttag gctggtgtta gggttctttg tttttggggt    60
ttggcagaga tgtgtttaag tgctgtggcc acatacccct c                       101

<210> SEQ ID NO 6
<211> LENGTH: 25
<212> TYPE: DNA
<213> ORGANISM: Artificial Sequence
<220> FEATURE:
<223> OTHER INFORMATION: Probe No. 1 Europium labeled

<400> SEQUENCE: 6
ggccacagca cttaaacaca tctct                                          25

<210> SEQ ID NO 7
<211> LENGTH: 25
<212> TYPE: DNA
<213> ORGANISM: Artificial Sequence
<220> FEATURE:
<223> OTHER INFORMATION: Probe No. 2 biotinylated

<400> SEQUENCE: 7
gaaccctaac accagcctaa ccaga                                          25

<210> SEQ ID NO 8
<211> LENGTH: 20
<212> TYPE: DNA
<213> ORGANISM: Artificial Sequence
<220> FEATURE:
<223> OTHER INFORMATION: Probe No. 3 biotinylatd

<400> SEQUENCE: 8
acaaagaacc ctaacaccag                                                20

<210> SEQ ID NO 9
<211> LENGTH: 22
<212> TYPE: DNA
<213> ORGANISM: Artificial Sequence
<220> FEATURE:
<223> OTHER INFORMATION: Probe No. 4 Europium labeled

<400> SEQUENCE: 9
aacacatctc tgccaaaccc ca                                             22

<210> SEQ ID NO 10
<211> LENGTH: 25
<212> TYPE: DNA
<213> ORGANISM: Artificial Sequence
<220> FEATURE:
<223> OTHER INFORMATION: Probe No. 5 biotinylated

<400> SEQUENCE: 10
ggccacagca cttaaacaca tctct                                          25

<210> SEQ ID NO 11
<211> LENGTH: 19
<212> TYPE: DNA
<213> ORGANISM: Artificial Sequence
<220> FEATURE:
<223> OTHER INFORMATION: Probe No. 6 biotinylated

<400> SEQUENCE: 11
taactatcaa accctatgt                                                 19
```

```
<210> SEQ ID NO 12
<211> LENGTH: 19
<212> TYPE: DNA
<213> ORGANISM: Artificial Sequence
<220> FEATURE:
<223> OTHER INFORMATION: Probe No. 7 conjugated to ATTO647N

<400> SEQUENCE: 12
aacttgaaag acatataat                                                19

<210> SEQ ID NO 13
<211> LENGTH: 22
<212> TYPE: DNA
<213> ORGANISM: Artificial Sequence
<220> FEATURE:
<223> OTHER INFORMATION: Probe No. 8 biotinylated

<400> SEQUENCE: 13
aacacatctc tgccaaaccc ca                                            22

<210> SEQ ID NO 14
<211> LENGTH: 25
<212> TYPE: DNA
<213> ORGANISM: Artificial Sequence
<220> FEATURE:
<223> OTHER INFORMATION: Probe No. 9 conjugated to ATTO647N or Alexa647

<400> SEQUENCE: 14
ggccacagca cttaaacaca tctct                                         25

<210> SEQ ID NO 15
<211> LENGTH: 25
<212> TYPE: DNA
<213> ORGANISM: Artificial Sequence
<220> FEATURE:
<223> OTHER INFORMATION: Probe No. 10 conjugeted to ATTO647N or Alexa647

<400> SEQUENCE: 15
gaaccctaac accagcctaa ccaga                                         25

<210> SEQ ID NO 16
<211> LENGTH: 20
<212> TYPE: DNA
<213> ORGANISM: Artificial Sequence
<220> FEATURE:
<223> OTHER INFORMATION: Probe No. 11 conjugated to ATTO647N or Alexa647

<400> SEQUENCE: 16
acaaagaacc ctaacaccag                                               20

<210> SEQ ID NO 17
<211> LENGTH: 22
<212> TYPE: DNA
<213> ORGANISM: Artificial Sequence
<220> FEATURE:
<223> OTHER INFORMATION: Probe No. 12 conjugated to ATTO647N or Alexa647

<400> SEQUENCE: 17
aacacatctc tgccaaaccc ca                                            22

<210> SEQ ID NO 18
<211> LENGTH: 22
<212> TYPE: DNA
<213> ORGANISM: Artificial Sequence
<220> FEATURE:
<223> OTHER INFORMATION: Probe No. 13 biotinylated
```

```
<400> SEQUENCE: 18
aacacatctc tgccaaaccc ca                                                  22

<210> SEQ ID NO 19
<211> LENGTH: 22
<212> TYPE: DNA
<213> ORGANISM: Artificial Sequence
<220> FEATURE:
<223> OTHER INFORMATION: Probe No. 14 Europium labeled

<400> SEQUENCE: 19
aacacatctc tgccaaaccc ca                                                  22

<210> SEQ ID NO 20
<211> LENGTH: 22
<212> TYPE: DNA
<213> ORGANISM: Artificial Sequence
<220> FEATURE:
<223> OTHER INFORMATION: Probe No. 15 Europium labeled

<400> SEQUENCE: 20
cacatctctg ccaaacccca aa                                                  22

<210> SEQ ID NO 21
<211> LENGTH: 99
<212> TYPE: DNA
<213> ORGANISM: Artificial Sequence
<220> FEATURE:
<223> OTHER INFORMATION: sequence of top strand of DNA transcription
      template

<400> SEQUENCE: 21
ggcgggagaa gaatttgaaa tctggttagg ctggtgttag ggttctttgt ttttggggtt         60
tggcagagat gtgtttaagt gctgtggcca gaagcgggg                                99

<210> SEQ ID NO 22
<211> LENGTH: 114
<212> TYPE: DNA
<213> ORGANISM: Artificial Sequence
<220> FEATURE:
<223> OTHER INFORMATION: sequence of bottom strand of DNA transcription
      template

<400> SEQUENCE: 22
ccccgcttct ggccacagca cttaaacaca tctctgccaa accccaaaaa caaagaaccc         60
taacaccagc ctaaccagat ttcaaattct tctcccgcct tttttcccgg cggc             114
```